United States Patent
Cha et al.

(10) Patent No.: US 11,891,529 B2
(45) Date of Patent: Feb. 6, 2024

(54) INK COMPOSITION FOR BIOPRINTING AND HYDROGEL FORMED FROM THE SAME

(71) Applicant: UNIST(ULSAN NATIONAL INSTITUTE OF SCIENCE AND TECHNOLOGY), Ulsan (KR)

(72) Inventors: Chaenyung Cha, Ulsan (KR); Jisu Hong, Ulsan (KR)

(73) Assignee: UNIST(ULSAN NATIONAL INSTITUTE OF SCIENCE AND TECHNOLOGY), Ulsan (KR)

( * ) Notice: Subject to any disclaimer, the term of this patent is extended or adjusted under 35 U.S.C. 154(b) by 697 days.

(21) Appl. No.: 16/816,079

(22) Filed: Mar. 11, 2020

(65) Prior Publication Data

US 2020/0291253 A1 Sep. 17, 2020

(30) Foreign Application Priority Data

Mar. 12, 2019 (KR) ........................ 10-2019-0028270

(51) Int. Cl.
| | |
|---|---|
| *C08F 2/46* | (2006.01) |
| *C08F 2/50* | (2006.01) |
| *C08G 61/04* | (2006.01) |
| *C09D 11/107* | (2014.01) |
| *C12M 1/12* | (2006.01) |
| *C09D 11/101* | (2014.01) |
| *C12N 5/00* | (2006.01) |
| *C12N 5/071* | (2010.01) |

(52) U.S. Cl.
CPC .......... *C09D 11/107* (2013.01); *C09D 11/101* (2013.01); *C12M 25/14* (2013.01); *C12N 5/0012* (2013.01); *C12N 5/0602* (2013.01)

(58) Field of Classification Search
CPC .... C09D 11/107; C09D 11/101; C12M 33/00; C12M 33/2514; C12N 5/0012; C12N 5/0602; C08F 2/50; C08F 2/46; C08G 61/04
USPC ........ 435/397; 522/6, 71, 189, 184, 1; 520/1
See application file for complete search history.

(56) References Cited

FOREIGN PATENT DOCUMENTS

| CN | 109777198 | * | 5/2019 |
|---|---|---|---|
| KR | 101738356 | * | 5/2017 |
| KR | 101738356 B1 | | 5/2017 |
| KR | 10-2018-0112436 A | | 10/2018 |
| WO | WO2018/186611 A | | 11/2018 |

OTHER PUBLICATIONS

Ryu et al., KR101738356 Machine Translation, May 22, 2017 (Year: 2017).*
Unnamed inventor, CN 109777198 Machine Translation, May 21, 2019 (Year: 2019).*
Hong et al, Complex tuning of physical properties of hyperbranched polyglycerol-based bioink for microfabrication of cell-laden hydrogels, Feb. 1, 2019, Adf. Funct. Mater., 29, 1808750, 1-14 (Year: 2019).*
Office Action for Korean Patent Application No. 10-2019-0028270, dated Jul. 31, 2020 (w/English translation).
Hong, Jisu et al., "Complex Tuning of Physical Properties of Hyperbranched Polyglycerol-Based Bioink for Microfabrication of Cell-Laden Hydrogels," *Advanced Functional Materials*, 29(13): 1808750 (14 pgs.) (Mar. 2019).

* cited by examiner

*Primary Examiner* — Jessica Whiteley
(74) *Attorney, Agent, or Firm* — Klarquist Sparkman, LLP

(57) ABSTRACT

Provided are an ink composition for bioprinting and a hydrogel formed therefrom, wherein the ink composition: a monomer or macromer having a photocurable functional group; and acrylic hyperbranched polyglycerol (AHPG).

15 Claims, 43 Drawing Sheets

FIG. 7-3

|  | $L_{13}$ | 2 $L_{14}$ | T | D | DP | DB | $M_n$ |
|---|---|---|---|---|---|---|---|
| HPG 2K | 1 | 6.4 | 3.57 | 2.2 | 21.83 | 0.51 | 1752 |
| HPG 5K | 1 | 5.94 | 3.32 | 2.72 | 50.05 | 0.58 | 4553 |
| HPG 15K | 1 | 4.24 | 2.03 | 1.92 | 192.82 | 0.55 | 14418 |

INK COMPOSITION FOR BIOPRINTING AND HYDROGEL FORMED FROM THE SAME

CROSS-REFERENCE TO RELATED APPLICATION

This application claims the benefit of Korean Patent Application No. 10-2019-0028270, filed on Mar. 12, 2019, in the Korean Intellectual Property Office, the disclosure of which is incorporated herein in its entirety by reference.

BACKGROUND

1. Field

One or more embodiments relate to an ink composition for bioprinting.

2. Description of Related Art

There is a growing interest in engineering miniaturized soft biomaterials for such applications as complex tissue constructs and drug delivery systems, with the recent advancement in microfabrication technology, such as digital light processing (DLP), stereolithography (SLA), and extrusion-based dispensing. Often collectively termed as "bioprinting" or "biofabrication", this technology is deemed especially attractive for biomedical engineering applications, because, as the concept of personalized medicine being hailed as the future paradigm of medicine. It is becoming ever more critical to rapidly produce tissue constructs and drug delivery systems with desired architecture and resolution, while controlling the biological functions of engineered tissues and drug release kinetics.

However, the microfabrication of polymer-based materials has largely been focused on conventional thermoplastic materials, such as poly(lactic acid) (PLA) and acrylonitrile-butadiene-styrene (ABS) via high-temperature melt extrusion used primarily for structural support, which is not suitable for encapsulating sensitive biological entities for tissue engineering and drug delivery applications.

With the continued maturation of biofabrication technology, the focus is now shifting towards developing "bioinks." Bioinks can not only be converted to a solid structure upon printing in a timely manner via a suitable crosslinking scheme, but also the resulting structure provides protection and suitable microenvironment for the encapsulating species. For this reason, the biofabrication technology is actively recruited to engineer various hydrogel-based structures. Hydrogels are widely used as scaffolds to support cells and tissues for various applications in regenerative medicine. Their mechanical properties can be tuned to provide regulatory physical signals to optimize various cellular functions, while providing protection against harmful external environment. Furthermore, the hydrogels can be engineered to present cell-recognition molecules (e.g. ECM proteins, cell adhesion peptides) to enhance their affinity towards the polymeric network for attachment.

Earlier efforts of hydrogel biofabrication mostly relied on natural polymers that undergo rapid crosslinking to form hydrogels by physical crosslinking, allowing for fabrication via conventional extrusion-based dispensing systems. For example, alginate hydrogels could be printed by using the extruded alginate solution via crosslinking using calcium ions. Agarose hydrogels can be fabricated by lowering the temperature to induce the physical crosslinking of the extruded solution which is kept at liquid state at elevated temperatures prior to printing.

Although this type of fabrication is generally straightforward due to its simple crosslinking mechanisms, the same cannot be said for controlling their material properties. This is because, when any chemical modification is made to natural polymers to control the characteristics of hydrogel, the fluid mechanics and/or the crosslinking efficiency that are crucial elements for the microfabrication process could be inadvertently changed. More recently, due to the widespread use of various photocrosslinked hydrogels in biomedical applications, light curing-based printing systems such as DLP and SLA are increasingly employed to generate micrometer-scale hydrogel constructs made from commercially available monomers and macromers, such as acrylamide, methyl methacrylate, or sodium acrylate, to known polymers conjugated with photolabile functional groups, such as poly(ethylene glycol) diacrylate (PEGDA), methacrylic alginate, or methacrylic gelatin. With the relatively simple modification to impart photocrosslinking capability, it is more applicable to a variety of polymers than extrusion-based systems.

SUMMARY

One aspect is to provide a novel ink composition for bioprinting.

Another aspect is to provide a crosslinked hydrogel formed by irradiating light to the ink composition for bioprinting.

Additional aspects will be set forth in part in the description which follows and, in part, will be apparent from the description, or may be learned by practice of the presented embodiments of the disclosure.

One aspect provides an ink composition for bioprinting including
  a monomer or macromer having a photocurable functional group, and
  acrylic hyperbranched ployglycerol (AHPG)

Another aspect provides a crosslinked hydrogel formed by irradiating light to a ink composition for bioprinting, and
  the ink composition including: a monomer or macromer having a photocurable functional group; and AHPG.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 1-2 shows the control of crosslinking density of hydrogels depending on the degree of substitution (DS) of acrylate of AHPG, and FIGS. 1-3 to 1-6 show the change in shear viscosity of each material with shear rate;

FIGS. 2-1~2-9 show the elastic modulus (E) of poly(ethylenglycol)methacrylate (PEGMA) hydrogel and polyacrylamide (PAAm) hydrogel, each crosslinked with AHPG having various concentrations, molecular weights (2000 (2K), 5000 (5K), 15000 (15K) g mol$^{-1}$) and acrylate DS;

FIGS. 3-1~3-5 show elastic modulus (E) of hydrogels having various AHPG concentrations and acrylate DS;

FIGS. 4-1~4-8 show the cumulative drug release profile and the like of a drug encapsulated in a hydrogel;

FIG. 5-1 shows images of cells encapsulated in MGel-AHPG5K hydrogels having various acrylate DS (AHPG concentration ratio (ΦAHPG)=0.1), and FIGS. 5-2~5-7 show diagrams of viability and proliferation rates;

FIGS. 6-1~6-4 show diagrams schematically showing the microfabrication of AHPG-crosslinked hydrogel via DLP projection printing;

FIG. 7-1 shows, $^{13}$C-NMR spectrum, FIG. 7-2 shows $^1$H-NMR spectrum, and FIG. 7-3 shows the integrated value of the peaks corresponding to various molecular weights, in relation to HPG; and FIG. 8 shows the $^1$H-NMR spectrum of AHPG.

DETAILED DESCRIPTION

Figure 1:
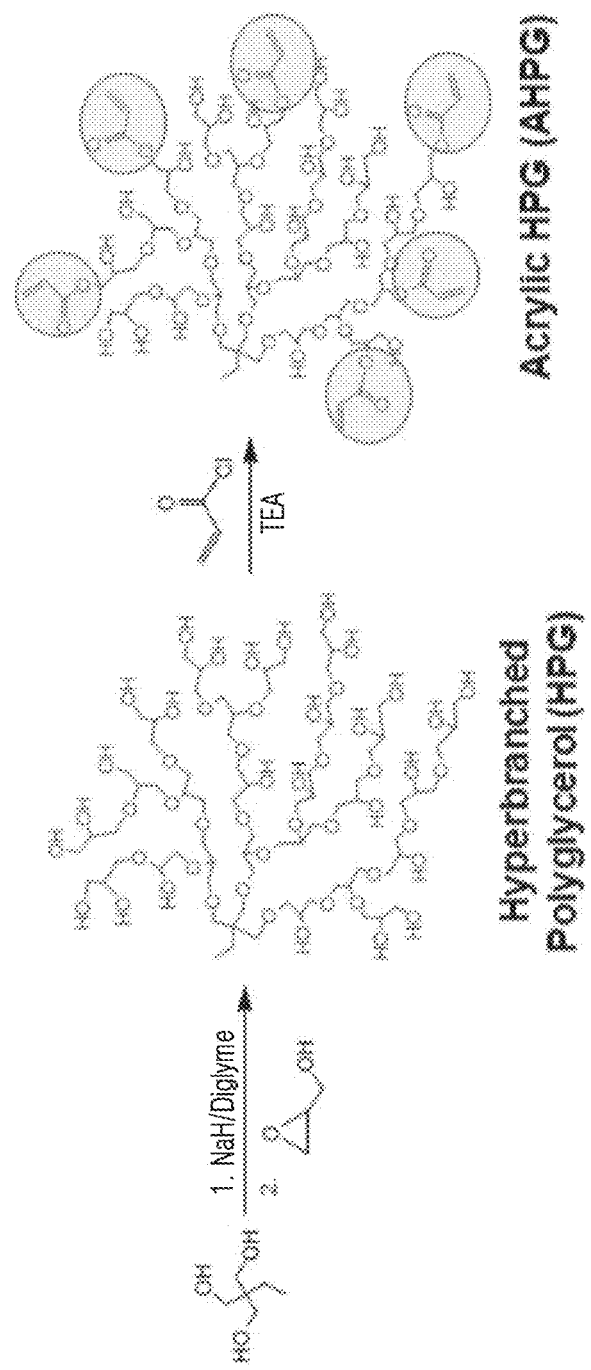
FIG. 1-1 shows synthesis of acrylic hyperbranched polyglycerol (AHPG) crosslinker.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

An ink composition for bioprinting according to one aspect includes: a monomer or macromer having a photocurable functional group; and acrylic hyperbranched ployglycerol (AHPG).

According to one embodiment, the concentration of AHPG in the ink composition for bioprinting may be from about 0.1% (w/v) to about 5% (w/v) based on the total volume of the ink composition. The concentration of AHPG may be from about 3% (w/v) to about 10% (w/v).

According to one embodiment, the concentration of the monomer or macromer having a photocurable functional group may be from about 1% (w/v) to about 30% (w/v) based on the total volume of the ink composition. The concentration of the monomer or macromer having a photocurable functional group may be from about 4% (w/v) to about 20% (w/v), for example, from about 4% (w/v) to about 15% (w/v), or from about 10% (w/v) to about 20% (w/v).

According to one embodiment, the concentration of the monomer or macromer having a photocurable functional group; and AHPG may be, based on the total volume, from about 5% (w/v) to about 30% (w/v), for example, from about 8% (w/v) to about 25% (w/v), or from about 5% (w/v) to 15% (w/v).

According to one embodiment, the molecular weight of AHPG may be from about 2000 Da to about 15000 Da, for example, about 2000 Da to about 10000 Da, or about 5000 Da to about 15000 Da.

According to one embodiment, a hyperbranched hydrogel glycerol moiety in the AHPG for the ink composition for bioprinting, may be prepared by reacting polyhydric alcohol with glycidol and may have a molecular weight of about 1700 Da to about 15000 Da, for example, about 1700 Da to about 10000 Da, or about 4000 Da to about 15000 Da. The polyhydric alcohol refers to a compound in which two or more OH groups are bonded to an alkyl group, and the polyhydric alcohol may be, for example, a trihydric alcohol or a tetrahydric alcohol. Non-limiting examples of the polyhydric alcohol include trimethylol ethane, trimethylol propane, pentaerythritol, di(trimethylol propane), and the like.

According to one embodiment, AHPG of the ink composition for bioprinting is prepared by reacting the OH end of the hyperbranched polyglycerol (HPG), prepared by reacting glycidol with polyhydric alcohol, with a compound having an acrylic group. In AHPG, 5 to 80% of the hyperbranched ployglycerol (OH) groups of HPG are substituted with an acrylic group. That is, the degree of substitution (DS) of the OH group of HPG by the acrylic group may be from about 5% to about 80%. For example, the DS may be from about 10% to about 70%.

According to one embodiment, the acrylic group may be acrylate or methacrylate.

The monomer having the photocurable functional group is not particularly limited, and according to one embodiment, the monomer having the photocurable functional group may be water-soluble, for example, acrylamide.

The molecular weight of the macromer having the photocurable functional group may be from about 400 Da to about 50000 Da.

The macromer having the photocurable functional group is not particularly limited and may be, for example, poly (ethylene glycol) methacrylate (PEGMA). The molecular weight of PEGMA may be from about 400 Da to about 5000 Da, for example, about 700 Da to about 2000 Da, or about 1000 Da to about 4000 Da. When the molecular weight of PEGMA is less than 400 Da, the solubility thereof with respect to aqueous solvents is significantly decreased, and when the molecular weight of PEGMA is greater than 5000 Da, the molecular fluidity is poor and the number of functional groups is reduced, thereby making gel formation difficult.

According to one embodiment, the water-soluble macromer having a photocurable functional group may be methacrylic gelatin (MGel). Methacrylic gelatin is gelatin bonded with a number of methacrylic groups, and a specific production method therefor is known, and thus will be omitted herein.

According to one embodiment, the ink composition may further include an aqueous solvent, and the aqueous solvent may be, for example, phosphate buffered saline (PBS) of pH 7.0 to pH 8.0, for example, 7.4.

According to one embodiment, the ink composition for bioprinting has a shear-thinning property. Therefore, when the ink composition is used as the ink of the 3D printer, since the ejection from the nozzle is smooth, the clogging phenomenon is significantly reduced, and the viscosity of the ejected ink returns to the viscosity before the ejection.

According to one embodiment, the ink composition may further include a photoinitiator, and the photoinitiator is not particularly limited, and according to one embodiment, may be 2-hydroxy-4'-(2-hydroxyethoxy)-2-methylpropiophenone.

According to another aspect, the hydrogel may be prepared by irradiating light to an ink composition for bioprinting to form crosslinking bonds, wherein the ink composition includes a monomer or macromer having a photocurable functional group and AHPG.

According to one embodiment, the ink composition for bioprinting may further include an aqueous solvent, and the aqueous solvent may be phosphate buffered saline (PBS).

According to one embodiment, the light may be ultraviolet (UV), and the wavelength of the UV may be from about 200 nm to about 450 nm, and the irradiation time may be from about 10 seconds to about 5 minutes. When the wavelength of the UV is less than 200 nm, the energy is too strong, and when the wavelength of the UV is more than 450 nm, the energy is too small to cause crosslinking. When the irradiation time is less than 10 seconds, crosslinking is not sufficiently achieved, and when it is more than 5 minutes, the irradiation time adversely affects drugs, cells, etc., which may be additionally added.

According to one embodiment, when the ink composition for bioprinting further includes a drug, the hydrogel may be used in a drug delivery system.

According to one embodiment, when the ink composition for bioprinting further includes a cell, the hydrogel may be used as a scaffold for cell culturing for tissue engineering for biomedical applications.

A hydrogel system based on a hyperbranched polyglycerol (HPG) crosslinker was developed in order to control the mechanical properties of hydrogels made from various monomeric systems in a more refined manner. HPG possesses several characteristics that are highly suited for biomedical applications, such as hydrophilicity, biocompatibility, and a simple synthetic route. In addition, the molecular weight and the degree of branching could also be easily controlled during the synthesis to tune the viscoelastic properties.

With numerous hydroxyl groups on a HPG molecule, it is also possible to control the degree of substitution (DS) of reactive functional groups required for crosslinking reaction. Here, a varying number of acrylate was bonded by a chemical reaction of hydroxyl groups on HPG to develop acrylic HPG (AHPG) to impart photocrosslinking capability. The effects of DS of acrylate, which in effect controls the hydrophilic/hydrophobic balance, and molecular weight of AHPG on the mechanical properties of resulting hydrogels were explored at various types of monomers to validate the necessity of tuning those physical properties of polymeric crosslinker for a particular monomer for optimal physical interaction that ultimately affect the hydrogel mechanics.

With this mechanical tunability as well as photocrosslinking capability, a DLP projection printing system was utilized to generate AHPG-crosslinked microgels (micrometer-sized hydrogel) with complex architecture and varying mechanical properties to demonstrate the AHPG-crosslinked hydrogel as versatile bioink material for bioprinting applications.

Synthesis of Photocrosslinkable AHPG

Figures 1, 2:
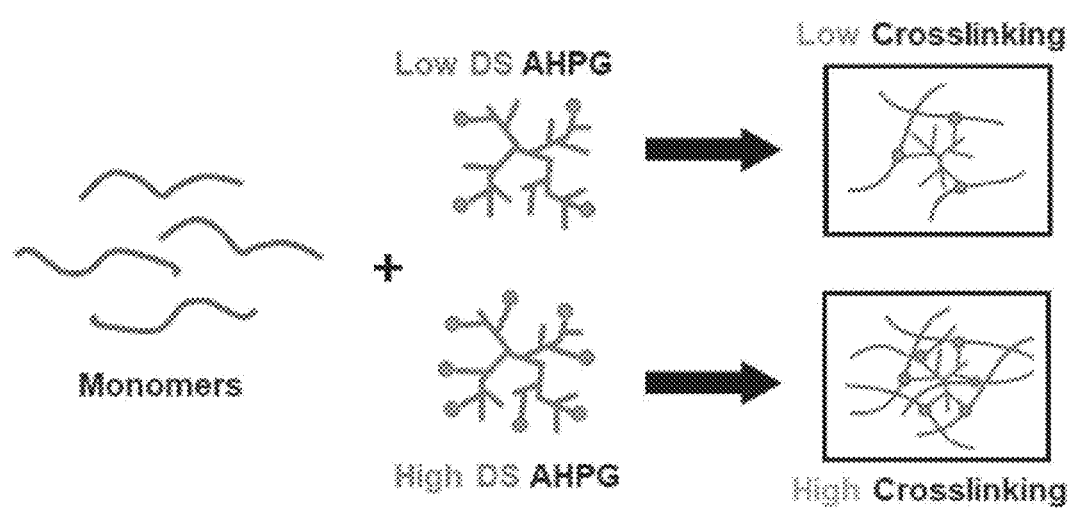

Unlike traditional dendrimers with precise molecular weight and well-defined shape, which are synthesized via sequential generation of branches (identified by the number of "generations"), hyperbranched polymers are developed by one-pot polymerization of monomers that generate random branching points, offering a more scalable and practical route for creating branched, multivalent macromolecules. HPG has garnered significant interest in the area of biomedical engineering, for their hydrophilicity and biocompatibility as well as their facile fabrication scheme. That is, HPG is generally considered a branched poly(ethylene glycol) due to its polyoxyether backbone. In addition, their multivalent hydroxyl groups provide an avenue for chemical modification to impart desired functionalities. Herein, HPGs having various molecular weights ($M_w$) were synthesized and their hydroxyl groups were bonded with photolabile acrylic groups. The acrylic HPG was then used as a multifunctional crosslinker to fabricate hydrogels with varying mechanical properties (FIG. 1-2). For conventional linear polymers, the number of functional groups are often limited, mostly to the end groups. On the other hand, branched polymers such as HPG contain numerous functional groups that could be converted to reactive functional groups in a given molecular weight. Moreover, the molecular dynamics of hyperbranched polymers would be less affected by the addition of the functional groups than linear polymers at the same molecular weight due to significantly less chain entanglement That is, the length of each chain on hyperbranched polymer is shorter than that of a linear polymer at the same $M_w$.

HPG was synthesized via anionic ring opening polymerization of glycidol as the monomer (FIG. 1-1). The $M_w$ could be controlled efficiently by the ratio of trimethylolpropane (TMP), to monomer. HPG with three different $M_w$ were synthesized; 1751, 4553, and 14 418 g mol$^{-1}$ as determined from $^3$C-NMR spectra, or 2230, 4350, and 14 300 as determined from gel permeation chromatography (GPC), which showed they are in good agreement. Herein, they are denoted as 2K, 5K, and 15K, respectively, for convenience. In addition, the ratio of TMP to base activator (i.e., NaH) was kept constant in order to keep the degree of branching constant, and only control the length of branches. Controlling the length of the branches of HPG was expected to modulate the interaction between the monomers (or macromers), resulting in various mechanical properties of the resulting hydrogels.

Figures 1, 2, 3:
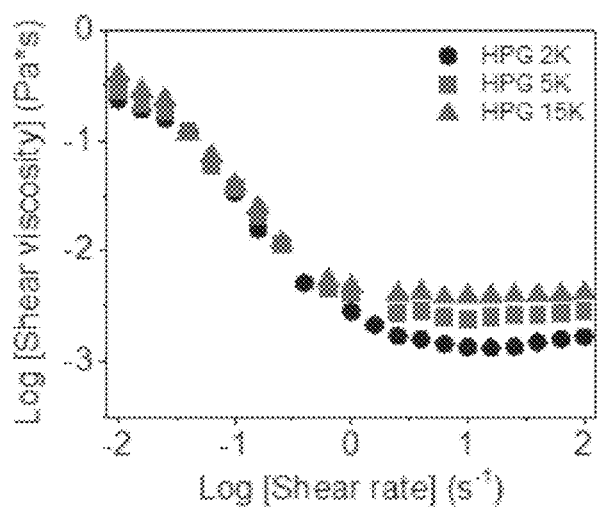

Controlling the $M_w$ of hyperbranched polymers such as HPG, as compared with linear polymers at the same range, was also expected to cause much smaller change in viscoelastic properties, which is an important factor for bioprinting applications where it is critical to control the fluid properties of ink materials. To evaluate the change in viscoelastic properties of HPG with varying $M_w$, the viscosity versus shear rate was measured. As a control, linear poly (ethylene glycol) (PEG) at similar $M_w$ were also investigated. With increasing shear rate, the distinctive shear-thinning behavior was shown for all HPG, in which there was a sharp decrease in shear viscosity when the shear rate was increased from 0.03 to 0.6 s$^{-1}$ for all HPG at the same rate (FIG. 1-3). In addition, the decrease occurred at the same region of shear rate. For linear PEG, on the other hand, the shear viscosity was generally higher at all shear rate, and the decrease with shear rate was more gradual (FIG. 1-4). Also, the viscosity at higher shear rate was more varied with $M_w$ than HPG. This result signified that the chain relaxation more readily occurred and the viscosity was less affected by the $M_w$ for HPG than the respective linear polymer, allowing for more extensive control of $M_w$ and concentrations of HPG without affecting the viscoelastic behavior.

FIG. 1-1 shows synthesis of acrylic hyperbranched polyglycerol (AHPG) crosslinker, FIG. 1-2 shows the control of crosslinking density of hydrogels depending on the degree of substitution (DS) of acrylate of AHPG, and FIGS. 1-3 to 1-6 show the change in shear viscosity of each material with shear rate.

FIG. 1-1 schematic diagram illustrating a process in which HPG was synthesized via anionic ring opening polymerization of glycidol as the monomer, and AHPG was obtained by nucleophilic reaction between hydroxyl groups of HPG and acryloyl chloride.

FIG. 1-2 shows a schematic view illustrating that the crosslinking density of hydrogels can be controlled by changing the degree of substitution (DS) of acrylate of AHPG.

FIG. 1-3 shows the measurements of the shear viscosity change with respect to the shear rate for HPG having a variety of $M_w$, and FIG. 1-4 shows the measurements of the shear viscosity change with respect to the shear rate for PEG with a variety of $M_w$. In FIGS. 1-3 and 1-4, the abscissa is the shear rate, and the ordinate is the shear viscosity.

FIG. 1-5 shows a graph of shear viscosity with respect to a shear rate, in relation to 20% (w/v) PEGMA-3% AHPG5K at varying acrylate DS, and FIG. 1-6 shows a graph of shear viscosity with respect to a shear rate, in relation to 20% (w/v) PEGMA-AHPG5K (DS3) with varying concentration. In FIGS. 1-5 and 1-6, the abscissa is the shear rate, and the ordinate is the shear viscosity.

Ultimately, HPG was bonded with varying number of acrylate to develop acrylic HPG ('AHPG') via nucleophilic substitution of the hydroxyl groups (FIG. 1-1). At a given $M_w$ of HPG, the DS of acrylate was controlled; 10, 30, 50, and 70% of the hydroxyl groups, which are denoted as DS1, DS2, DS3, and DS4, respectively, for convenience (FIG. 2-1~2-9). It was hypothesized that the mechanical properties of the hydrogels crosslinked with AHPG could be controlled with the acrylate DS, even without changing the concentration. This would also ensure that the viscoelastic properties of various precursor solutions could remain largely constant while trying to control the mechanical properties of resulting hydrogels with either $M_w$ of acrylate DS.

Mechanical Properties of AHPG-Crosslinked Hydrogels

Hydrogels crosslinked with AHPG were fabricated via photocrosslinking and their mechanical stiffness was measured to assess the effect of physical properties of AHPG, $M_w$ and acrylate DS, on the crosslinking reaction with different monomers, and subsequently the hydrogel mechanics. With the unconventional molecular architecture (i.e., hyperbranched), varying hydrophilic-hydrophobic balance arising from acrylate DS (i.e., hydrophilic polyoxyethylene backbone and hydrophobic acrylate), it was hypothesized that the AHPG would have significant influence over different types of monomers. Therefore, hydrogels made from three different types of widely used monomers were investigated; small molecule (e.g., acrylamide), macromer (e.g., poly(ethylene glycol) methacrylate (PEGMA)), and protein (e.g., methacrylic gelatin (MGel)). The hydrogel stiffness was evaluated by calculating compressive elastic moduli.

FIGS. 2-1 to 2-6 show diagrams of elastic moduli (E) of PEGMA hydrogels crosslinked with AHPG having varying concentrations and acrylate DS, and FIGS. 2-7 to 2-9 show diagrams of elastic moduli (E) of PAAm hydrogel crosslinked with AHPG having varying concentrations and acrylate DS.

The $M_w$ of AHPG are (in FIGS. 2-1, 2-4, and 2-7) 2K, (in FIGS. 2-2, 2-5, and 2-8) 5K, and (in FIGS. 2-3, 2-6, and 2-9) 15K. The concentrations of PEGMA for FIGS. 2-1 to 2-3 are 10% (w/v), and the concentrations of PEGMA for FIGS. 2-4 to 2-6 are 20% (w/v). The concentrations of PAAm for FIGS. 2-7 to 2-9 are 20% (w/v). In FIGS. 2-1 to 2-9, the abscissa represents the DS of acrylate, and the ordinate represents the modulus.

Macromer: Poly(Ethylene Glycol) Monoacrylate (PEGMA)

First, PEGMA hydrogels crosslinked with AHPG were developed and their elastic moduli were obtained (FIGS. 2-1 and 2-3). The concentration of PEGMA was controlled at 10% (w/v), while that of AHPG was controlled from 0.5 to 3% (w/v) for 10% (w/v) PEGMA, or from 1% (w/v) to 5% (w/v) for 20% (w/v) PEGMA. At low $M_w$ AHPG at 2K, hydrogels did not form until acrylate DS of AHPG was increased to DS3, and the elastic moduli were larger at DS4 than DS3 (FIG. 2-1). On the other hand, at AHPG5K, the elastic moduli of hydrogels were generally larger and the hydrogels formed at lower concentration and acrylate DS than AHPG2K (FIG. 2-2). This suggested that at the given concentration, significant branch length was required to interact with the macromer chains leading to enhanced crosslinking efficiency. It should be emphasized that compared to linear polymer at the same $M_w$, hyperbranched polymers are more compact and thus less likely to physically interact with other polymer chains. Interestingly, there was a decrease in moduli when the acrylate DS was increased beyond a certain value; DS4 for 3% (w/v) and DS3 for 1% (w/v). With increasing hydrophobicity at higher acrylate DS, diminished physical association between hydrophilic macromer may have reduced the extent of crosslinking reaction. When the $M_w$ of AHPG was further increased to 15K, there was an increase in moduli up to DS2, especially at 3% AHPG (FIG. 2-3). However, the elastic moduli decreased more sharply at higher acrylate DS, suggesting that the increased hydrophobicity with AHPG with higher acrylate DS likely caused insufficient physical association between PEGMA and AHPG, more so at higher $M_w$ with decreased chain conformational flexibility and mobility, further diminishing the extent of crosslinking. This explanation was further corroborated by the increased opaqueness and microscopic heterogeneity shown for hydrogels crosslinked with AHPG at higher acrylate DS and concentration, which suggested there was significant phase separation within the hydrogel network. These results not only demonstrate the control of mechanical properties of hydrogels with AHPG, but also highlight the importance of considering the physical properties of the AHPG crosslinkers, namely, the chain length and hydrophilic-hydrophobic balance, when choosing the macromer condition for preparing hydrogels.

Figures 1, 2, 3, 4:
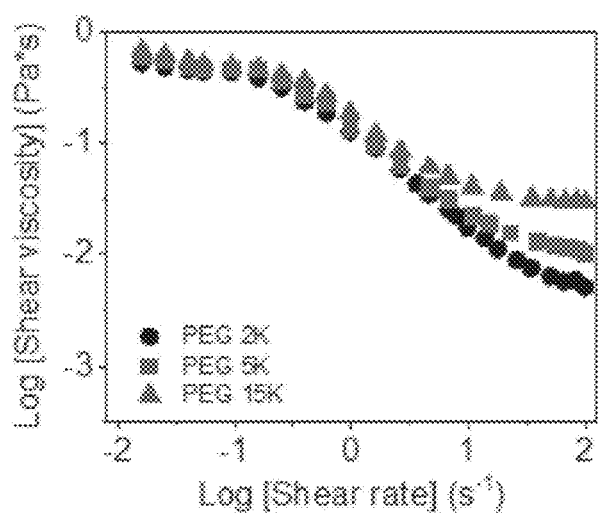

When the concentration of PEGMA was increased to 20% (w/v), the range of elastic moduli was much greater, and the hydrogels formed even at lower acrylate DS and concentrations of AHPG than the hydrogels at 10% (w/v) PEGMA (FIGS. 2-4 and 2-6). With AHPG2K, the hydrogel formed at all acrylate DS and the elastic moduli increased with acrylate DS at all concentrations, from 1 to 5% (FIG. 2-4). In addition, there was much greater increase in moduli at higher $M_w$ of AHPG, 5K and 15K, by the acrylate DS and concentration than those at 10% PEGMA hydrogels (FIGS. 2-5 and 2-6). These results demonstrated that the branched polymeric chains of AHPG could extensively incorporate the increased amount of macromers to form the hydrogel network. Similar to 10% (w/v) PEGMA hydrogels, the elastic moduli decreased above a critical acrylate DS at higher concentration and $M_w$ of AHPG, further confirming the role of diminished chain movement and increased hydrophobicity on the extent of crosslinking between PEGMA and AHPG.

The viscosity versus shear rate curves for the PEGMA-AHPG hydrogel precursor solutions were measured to assess the effects of $M_w$ and concentration of AHPG on their fluid behavior (FIGS. 1-5 and 1-6). The changes in viscosity in response to varying shear rate were not significantly affected, and the well defined shear-thinning behavior was demonstrated, regardless of the $M_w$ and acrylate DS of AHPG. This result further established that the use of hyperbranched polymeric crosslinker could control the mechanical properties of hydrogels with consistent fluid properties with shear-thinning behavior, validating AHPG as an effective ink material for microfabrication.

Small Molecular Monomer: Acrylamide

Polyacrylamide (PAAm) hydrogels, prepared by copolymerization between acrylamide monomers and crosslinkers, have long been utilized in various biomedical applications, such as gel electrophoresis, medical implants, and drug delivery systems. Thus, AHPG was further investigated as a crosslinker for acrylamide monomers to fabricate PAAm hydrogels, and their mechanical properties were evaluated (FIGS. 2-7 and 2-9). For AHPG2K and AHPG5K, the range of elastic moduli controlled by the AHPG concentration was similar, and the minimum acrylate DS for hydrogel fabrication was the same at DS2 (FIGS. 2-7 and 2-8). This result suggested the small molecular monomers such as acrylamide having greater mobility than larger macromers could more readily interact with AHPG crosslinkers, such that the change in $M_w$ of AHPG within this range did not have a significant effect on the crosslinking.

When the $M_w$ of AHPG was further increased to 15K, there was a drastic decrease in mechanical properties at all concentrations and acrylate DS by more than 50%, up to 80% (FIG. 2-9). This significant drop may have been due to the larger size of AHPG disrupting the PAAm chain growth, the process that was not necessary for the macromers such as PEGMA, which already possessed polymeric chain structure. From the standpoint of AHPG, it is plausible that the limited conformational and translational mobility of longer chains of AHPG favored self-association via chain entanglement rather than interaction with growing PAAm chains. This was further strengthened by the fact that the elastic moduli were the highest at DS1 and decreased with acrylate DS, which likely resulted from the separation of AHPG with higher acrylate DS from growing PAAm chains due to increased hydrophobicity.

Multivalent Macromer: Methacrylic Gelatin

FIGS. 3-1 and 3-2 show diagrams of elastic moduli (E) of MGel hydrogel having acrylate DS at 4% (w/v) MGel, and at varying concentrations of AHPG from 0.1% (w/v) to 1% (w/v), and FIGS. 3-3 and 3-4 show diagrams of elastic moduli (E) of MGel hydrogel having acrylate DS when the total polymer concentration was kept constant at 10% (w/v), while varying the fraction of AHPG (ΦAHPG). The $M_w$ of AHPG is 2K in FIG. 3-3, 5K in FIGS. 3-1 and 3-4, and 15K in FIGS. 3-2 and 3-5.

Polymers having multiple functional groups on the backbone can be bonded with crosslinkable functional groups in a varying degree of substitution. This type of "multivalent" polymers can either form hydrogel by themselves above a critical concentration, or be crosslinked or hybridized with another crosslinker to form hydrogels at a lower concentration. To further evaluate the crosslinking ability of AHPG, photocrosslinkable gelatin which contains multiple methacrylic groups (MGel) as a model macromer was crosslinked with AHPG to develop hydrogels, and their mechanical properties were similarly evaluated (FIG. 5-1~5-7). Photocrosslinkable MGel-based hydrogels are widely used as scaffold materials for tissue engineering applications. With the amphiphilic nature of gelatin as a protein, it also suggested that the acrylate DS of AHPG could also play a significant role in controlling the hydrogel mechanics.

The average molecular weight of MGel may range from about 400 Da to about 50000 Da, for example, 3000 Da to 50000 Da, for example, 10000 Da to 40000 Da.

First, the concentration of MGel was kept at 4% (w/v), which is below the critical concentration for hydrogel formation by itself (5% (w/v)), and the concentration of AHPG was controlled from 0.5% (w/v) to 3% (w/v) in order to evaluate AHPG purely as a crosslinker (FIGS. 3-1 and 3-2). Interestingly, the hydrogels did not form at all conditions when the $M_w$ of AHPG was 2K. For 5K AHPG, the hydrogels did form at all conditions, but the elastic moduli were very low, all below 1 kPa, and were not significantly affected by the concentration and acrylate DS of AHPG, demonstrating insufficient crosslinking density (FIG. 3-1). When the $M_w$ of AHPG was increased to 15K, there was significant increase in the elastic moduli, and their dependence on AHPG concentration and acrylate DS (FIG. 3-2). These results highlight the importance of extensive physical interaction between two polymeric systems in order to maximize the extent of crosslinking reaction; longer branches could more extensively associate with MGel chains leading to more efficient crosslinking reaction.

Alternatively, the total polymer concentration was kept constant at 10% (w/v), while varying the fraction of AHPG ($\Phi_{AHPG}$) from 0.1 to 0.3. For AHPG2K, the elastic moduli expectedly increased with acrylate DS for all $\Phi_{AHPG}$ (FIG. 3-3). However, the elastic moduli decreased with $\Phi_{AHPG}$ at all acrylate DS. On the other hand, for AHPG5K, the elastic moduli were greater than those for AHPG2K-crosslinked hydrogels, and they increased with $\Phi_{AHPG}$ from 0.1 to 0.2 at all acrylate DS (FIG. 3-4), suggesting the increased chain length of AHPG helped improve the physical interaction with MGel leading to greater degree of crosslinking. Though it should be noted that at the highest $\varphi_{AHPG}$ of 0.3, the elastic modulus did not continuously increase with acrylate DS, rather showed a decrease above DS3, pointing to the adverse effect of significant increase in hydrophobicity on the extent of crosslinking. As with AHPG2K, except for the highest modulus achieved with AHPG5K (DS4) at $\Phi_{AHPG}$☐☐☐0.2, the elastic moduli of all the other conditions were lower than the elastic modulus of pure MGel hydrogel at the same polymer concentration of 10% (w/v) (4.5 kPa). This showed that even at higher $M_w$, the crosslinking reaction between MGel and AHPG5K was not as effective as that of MGel by itself, suggesting there was insufficient physical association between MGel and AHPG5K.

Figures 1, 2, 3, 4, 5:
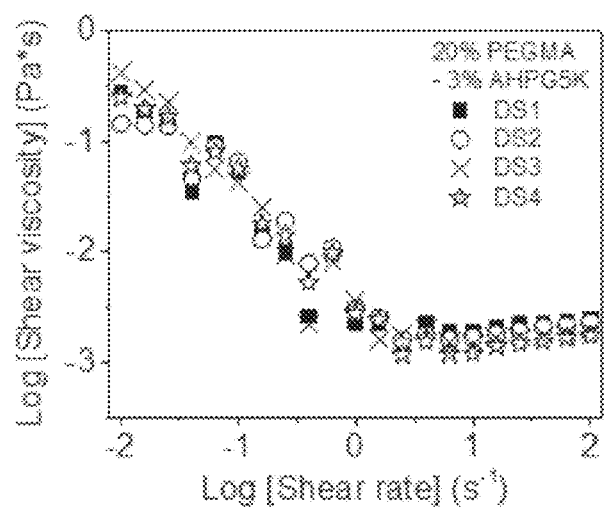

Surprisingly, the elastic moduli of hydrogels crosslinked with AHPG15K were markedly larger than those with AHPG5K at all conditions; up to 6-fold increase at DS1, 20-fold increase at DS2, and 10-fold increase at DS3, clearly demonstrating the effect of chain length (FIG. 3-5). The increase in the elastic moduli from DS1 to DS2 demonstrated the effect of increased crosslinking density with higher number of acrylate groups. In addition, the elastic moduli increased with $\Phi_{AHPG}$ at the DS2, indicating the increased portion of AHPG was able to stably mix with MGel without any noticeable phase separation. These results, compared with those of AHPG2K and 5K, demonstrated that the increased chain length of AHPG helped promote the physical association with MGel, leading to much greater degree of crosslinking reaction. It should be noted that the elastic moduli decreased significantly from DS2 to DS4 at all $\Phi_{AHPG}$, again highlighting the increased hydrophobicity disrupted their stable coexistence and prevented sufficient crosslinking. Furthermore, the viscosity of MGel-AHPG precursor solution was similarly not affected by the $M_w$ and acrylate DS of AHPG and shear-thinning behavior was demonstrated.

Taken all together, the mechanical properties of the AHPG-crosslinked hydrogels revealed the importance of physical properties of the crosslinking polymer, controlled by the $M_w$ and hydrophobicity, in dictating the extent of crosslinking for different monomeric systems, while maintaining the viscoelastic properties of precursor solutions.

Diffusional Properties of AHPG-Crosslinked Hydrogels

FIGS. 4-1 to 4-4 show cumulative drug release profiles ($M_t/M_\infty$) of PAAm-AHPG5K hydrogel and PEGMA-AHPG5K hydrogel. FIGS. 4-1 and 4-2 show the profiles of PAAm-AHPG5K hydrogel with varying acrylate DS at the same concentration (3% (w/v)) or with varying concentration at the same DS (FIGS. 4-1 and 4-2), and FIGS. 4-3 and 4-4 show the profiles of PEGMA-AHPG5K hydrogel with varying acrylate DS at the same concentration (3% (w/v)) or with varying concentration at the same DS. FIGS. 4-5 to 4-8 show that the kinetic rate constants (k) and the exponents (n)

were obtained by fitting the profiles in FIGS. 4-1 to 4-4 with diffusion-based Ritger-Peppas model.

The swelling ratios of the PEGMA, PAAm, and MGel hydrogels crosslinked with various AHPG were measured, and it was confirmed that the changes in swelling ratio were well correlated inversely with the corresponding moduli shown in FIGS. 2-1~2-9 and 4-1~4-8. According to the rubber-elasticity theory, such results demonstrate the polymeric networks created by crosslinking with AHPG were highly elastic. To further characterize the diffusional properties of the AHPG-crosslinked hydrogels, time-dependent drug release behavior from the AHPG-crosslinked hydrogels was measured. Bovine serum albumin (BSA) as a model protein was encapsulated in PEGMA or PAAm hydrogels crosslinked with AHPG at varying acrylate DS or concentration, and the amount of BSA release was measured over time.

For PAAm-AHPG hydrogels, the release profiles (i.e., cumulative release vs time) showed the expected dependence on the crosslinking density of the hydrogels, in which the release rate constants (k) decreased with increasing crosslinking density, either via acrylate DS (FIGS. 4-1 and 4-5) or concentration (FIGS. 4-2 and 4-6), indicating that both methods were effective in modulating the release of encapsulated drugs by controlling the mesh size of the polymeric network. For PEGMA hydrogels, similar control of drug release was demonstrated by controlling the acrylate DS of AHPG (FIGS. 4-3 and 4-7). However, the drug release rate rather increased when the concentration of AHPG was increased from 1% (w/v) to 5% (w/v), which was opposite to the result shown for PAAm-AHPG hydrogels (FIGS. 4-4 and 4-8). This interesting result may have stemmed from the hydrophilic and antifouling properties of PEGMA coupled with the increasing amount of AHPG having similar properties (i.e., HPG is considered a branched PEG) helped facilitate the release of protein drug. In both hydrogel systems, the exponents (n) were consistently in between 0.2 and 0.3 regardless of the type of macromer and the DS and concentration of AHPG, signifying the quasi-Fickian diffusion in which there was less time dependence and greater initial burst release owing to their hydrophilicity than typical drug release behavior from hydrogels that are generally governed by Fickian diffusion.

Overall, the drug release behavior from AHPG-crosslinked hydrogels highlighted that the physical properties of AHPG itself (e.g., hydrophilicity, branched morphology) largely dictated the drug release mechanism, and further demonstrate their capability as a drug delivery system with tunable release rates.

Biocompatibility of AHPG-Crosslinked Hydrogels

Figures 1, 2, 3, 4, 5, 6:
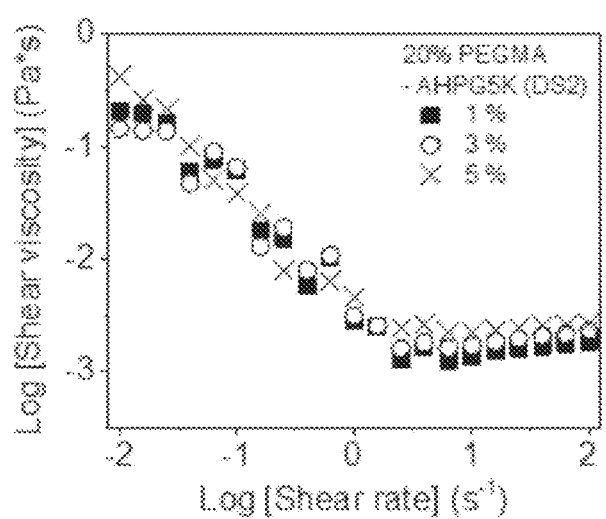

FIG. 5-1 shows optical and fluorescent microscopic images of MSCs (left) and MCF-7 cells (right) encapsulated in MGel-AHPG5K hydrogel with varying acrylate DS ($\Phi_{AHPG}$=0.1). The cells were labeled with fluorescent probes to identify live (green) and dead (red) cells. FIGS. 5-2 and 5-5 show the cell viability at various times during culture up to day 7, and FIGS. 5-3 and 5-6 show the measurements of the normalized numbers of viable cells ($N_t/N_0$) over time ($N_t$: number of viable cells at time, t, $N_0$: number of initial viable cells). FIGS. 5-4 and 5-7 show that the plots in (c) and (f) were fitted with a power-law model to obtain the proliferation rates ($k_P$) (*$p<0.05$, n=6).

The application of AHPG-crosslinked hydrogel as a cell culture platform for tissue engineering was investigated by encapsulating the cells within the AHPG-crosslinked hydrogels with varying acrylate DS and concentration and measuring their viability and proliferation. Here, MGel hydrogels crosslinked with AHPG were used because gelatin provides cell-adhesive and degradation properties necessary for cellular activities. Two different cell types, mesenchymal stem cells (MSCs) and breast carcinoma cells (MCF-7), were encapsulated in MGel-AHPG5K hydrogels with varying acrylate DS. The total polymer concentration was 10%, while controlling the fraction of AHPG, $\Phi_{AHPG}$, to be either 0.1 or 0.2.

Regardless of the cell type, the viability of encapsulated cells remained high (above 80%) throughout the culture period (FIGS. 5-1, 5-2, and 5-5), demonstrating the biocompatibility of this hydrogel system regardless of the crosslinking density controlled by the acrylate DS. However, the effect of mechanical properties of hydrogel on the proliferation was more dependent on the cell type. For MSCs, the proliferation was biphasic; the proliferation rate ($k_P$) was greater at the lower DS (DS1) and the higher DS (DS3), and lower at intermediate DS (DS2) and the highest DS (DS4) (FIGS. 5-3 and 5-4). The greater proliferation at lower acrylate DS (DS1) was likely attributed to the increased media perfusion and availability of space, while increased mechanical rigidity at higher acrylate DS (DS3) promoted the proliferation via mechanotransdudion despite lower permeability of hydrogel. But this mechanical effect could not compensate for further decrease in hydrogel permeability at the highest acrylate DS (DS4), leading to diminished proliferation.

Figures 1, 2:
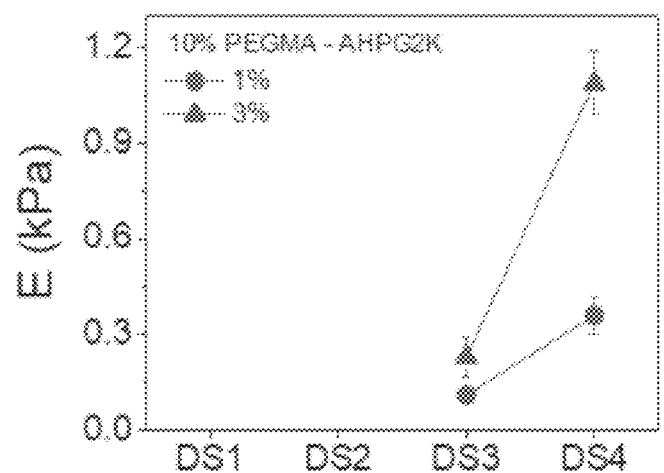
Figure 2:
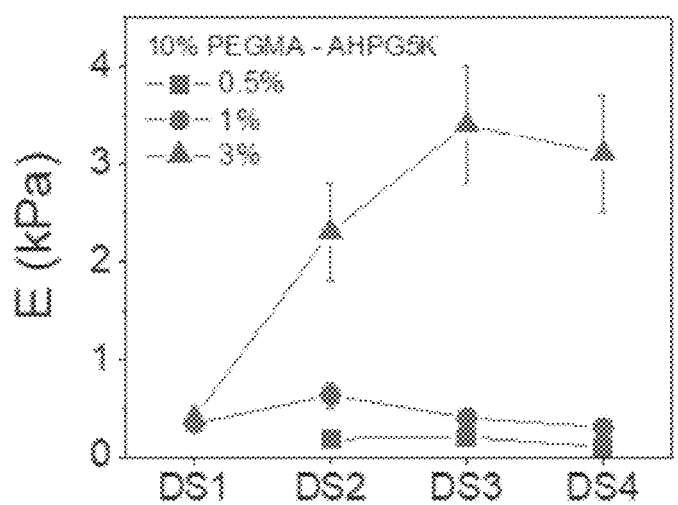
Figures 2, 3:
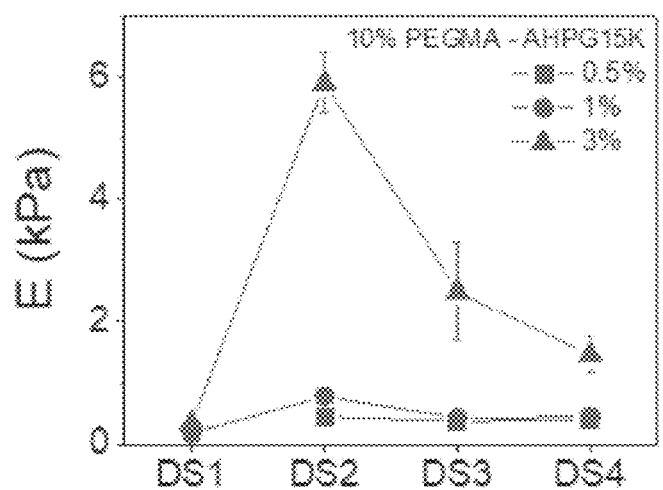
Figures 2, 3, 4:
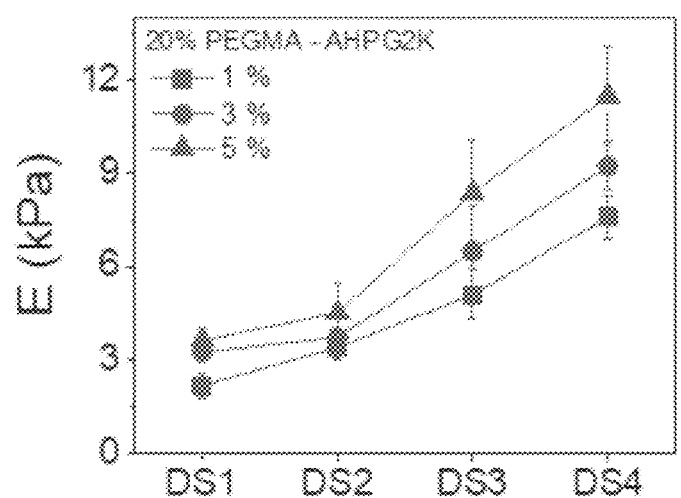
Figures 2, 3, 4, 5:
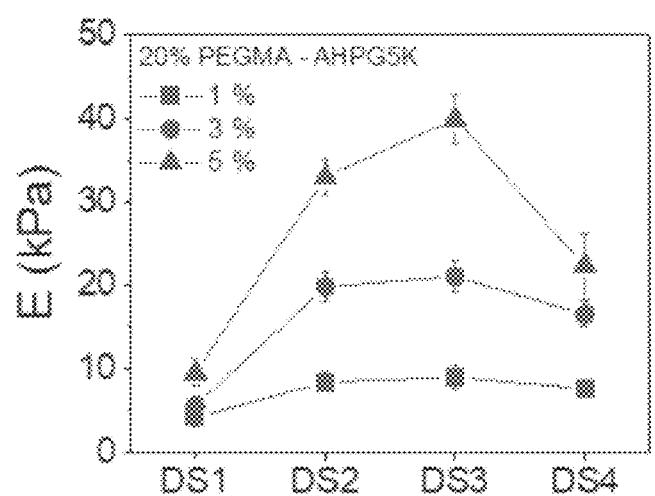
Figures 2, 3, 4, 5, 6:
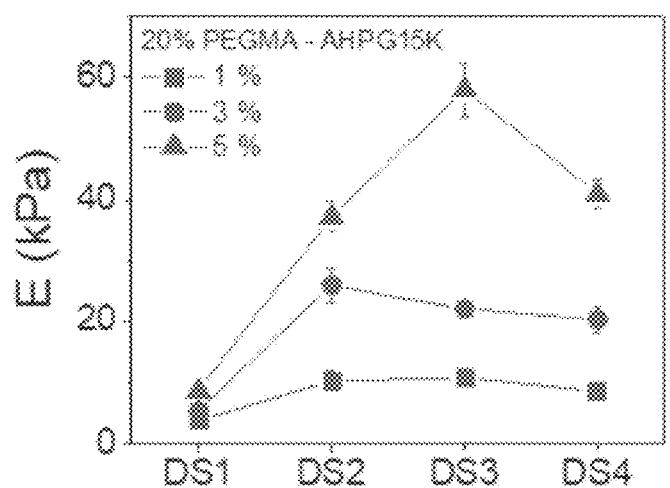
Figures 2, 3, 4, 5, 6, 7:
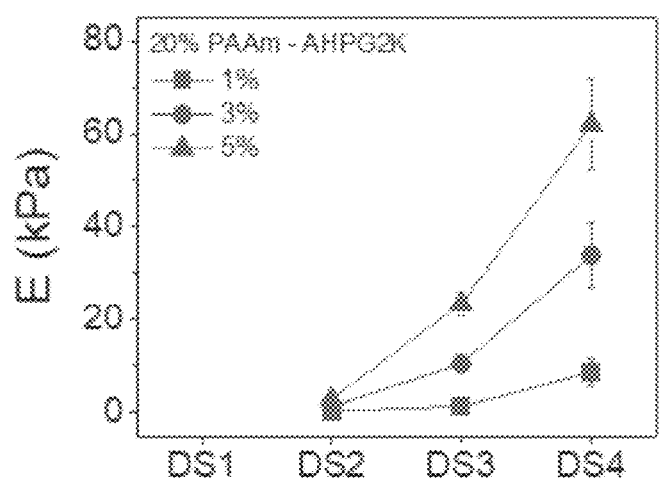

Interestingly, MCF-7 cells showed different proliferation behavior under the same hydrogel conditions. The trend in proliferation rate ($k_P$) was opposite to that of MSCs; the $k_P$ was maximal at DS2, and decreased at both lower (DS1) and higher (DS3, DS4) acrylate DS (FIGS. 5-6 and 5-7). The fact that the proliferation was not enhanced at lower acrylate DS and similar to that at higher acrylate DS indicated that increased diffusion and available space may not have been as significant a factor for promoting proliferation. The substantial increase in $k_P$ from DS1 to DS2 suggested that the increased mechanical properties promoted the proliferation of MCF-7 cells, but subsequent decrease in $k_P$ with increasing acrylate DS also suggested that there is an optimal mechanical environment for their proliferative capacity. The decrease in $k_P$ at DS3 and DS4 also suggested that the cells were also highly sensitive to diminished permeability of the hydrogels. The same in vitro studies were performed using MGel hydrogels crosslinked with AHPG at higher $\Phi_{AHPG}$ of 0.2. The viability was well maintained regardless of the gel conditions, and the similar biphasic trends in $k_P$ were also demonstrated. However, the $k_P$ values were generally lower at all conditions, likely due to the diminished permeability and available space for cellular growth at higher $\Phi_{AHPG}$.

Microfabrication of Cell-Laden Microgels Via DLP Projection Printing

FIG. 6-1 shows microfabrication of AHPG-crosslinked hydrogels via DLP projection printing. FIG. 6-2 shows that the DLP printing allows the fabrication of microgels with various shapes and FIG. 6-3 shows that numerous arrays can be made by using the DLP printing. FIG. 6-4 shows that the microgel architecture was well maintained regardless of mechanical properties controlled by acrylate DS of AHPG.

The AHPG-based hydrogel according to one embodiment of the present disclosure can be viewed as an ideal bioink material. In addition, the consistent fluid properties of precursor solutions could also allow the control of mechanical properties of hydrogels without significantly affecting their printability.

Herein, DLP-based projection printing apparatus was employed to create cell-laden AHPG-crosslinked hydrogel arrays having various shapes with micrometer-scale resolution to demonstrate the feasibility as mechanically tunable bioink to develop microtissue constructs (FIGS. 6-1~6-4). MGel-AHPG hydrogels with varying acrylate DS, as presented in FIGS. 5-1~5-7, were used. The DLP printing technology made use of a digital micromirror device (DMD) which is used to reflect the micropatterned UV light on to a sample stage mounted with the bioink through a microscopic lens (FIG. 6-1).

By controlling the positions of micromirrors, only the select pattern of a curing light is directed toward the sample, resulting in the fabrication of microgels with the same pattern. The MGel-AHPG microgels having various shapes with different complexities were successfully fabricated (FIG. 6-2). With the DMD technology capable of programmable automation processing, the fabrication was easily streamlined to develop multiple arrays of MGel-AHPG microgels in a single platform, while controlling their size, shape, and spacing, by adjusting the position of the sample stage during multiple fabrication steps, demonstrating efficient large-scale production value (FIG. 6-3). The shape and architecture of the microgels were well maintained regardless of the acrylate DS of AHPG (FIG. 6-4). To further demonstrate the printability of AHPG-crosslinked bioinks, PAAm-AHPG and PEGMA-AHPG microgels were similarity fabricated by the DLP printing. Although the initial microgel resolution was well maintained, a small distortion occurred over time due to the greater degree of swelling for PAAm and PEGMA hydrogels.

To evaluate the biocompatibility of AHPG-crosslinked hydrogels, cells were encapsulated in the MGel-AHPG microgel arrays and their viability and growth were evaluated. Regardless of acrylate DS, the cells within the microgels showed good biocompatibility, with the cell viability above 80% for all conditions. Also, the cells continue to proliferate over time within the microgels after day 4 of culture, the trend was similar to the result shown in FIGS. 5-1~5-7. It should be noted that unlike the cells in large-scale hydrogels in FIGS. 5-1~5-7, the cells could more readily migrate out of the much smaller microgels, and spread onto the surrounding tissue-culture area. This was more apparent at DS2 in which the proliferation was the highest, indicating the cell motility and proliferation were both promoted at this mechanical environment. This further suggested the cell-laden microgels could be utilized as an injectable form of tissue constructs.

That is, these results demonstrate the tunable mechanics of AHPG-crosslinked hydrogels, coupled with the efficiency of DLP-based printing, could generate many cell-laden microgel constructs for tissue engineering applications.

CONCLUSION

A physically tunable crosslinker based on HPG, namely, acrylic HPG (AHPG), was developed in order to control the mechanical properties of hydrogels prepared with different monomeric systems. The interaction between various monomers and macromers could be effectively modulated by controlling the $M_w$ and acrylate DS of AHPG, resulting in hydrogels with varying ranges of mechanical properties, highlighting the importance of physical properties of the crosslinking polymer in determining the hydrogel mechanics for different monomeric systems. This tunable mechanics of hydrogels imparted by the AHPG crosslinker was utilized as (1) drug delivery system capable of controlling the drug release rate and (2) 3D cell-culture platform providing variable mechanical microenvironment. Owing to the photocrosslinkability and tunable mechanics, the precursor solution for AHPG-crosslinked hydrogel was used as "bioink" to fabricate biocompatible cell-laden hydrogels with micrometer-scale resolution and architecture via DLP-based projection printing technology, demonstrating their potential as miniaturized tissue constructs for biomedical applications.

Taken together, it is expected that AHPG crosslinker with tunable $M_w$ and acrylate DS could provide a suitable platform for fabricating various hydrogel systems with varying mechanical properties and be applied as bioactive ink material for bioprinting applications.

The present disclosure is explained in more detail through the following examples. However, the examples are provided to illustrate the present disclosure, and do not limit the scope of the present disclosure.

EXAMPLES

Synthesis of AHPG

Trimethylol propane (TMP, 2 mmol, Sigma Aldrich) as the initiator was first activated by reaction with sodium hydride (0.5 mmol, 60% suspension in mineral oil, Sigma Aldrich) in dry diglyme (0.6 mL, Sigma Aldrich), to deprotonate the hydroxyl groups resulting in alkoxide formation. The hydroxyl groups in TMP were partially deprotonated in order to lower the polydispersity and prevent unwanted cyclization. Into this activated initiator, glycidol (Sigma Aldrich) as the monomer was slowly added via an electronic syringe pump (KDS Legato 100, KD Scientific) over 12 hours, and continuously stirred at 95° C. The mixture was further reacted at 95° C. for additional 3 hours after completing the monomer addition. Then, the mixture was cooled to 50° C. and hydrochloric acid (5 mmol) dissolved in 20 mL methanol (Samchun Chemicals, Korea) was added to quench the reaction. The crude product was obtained by three rounds of precipitation and washing in diethyl ether. HPGs with three different molecular weights ($M_w$) were prepared by varying the feed molar ratio of monomer (glycidol) to initiator (TMP): 13.5, 67.5, and 200. The chemical structure of HPG was confirmed by $^{13}$C-NMR spectroscopy (FIG. 7-1~7-3)

The degree of polymerization (DP), the degree of branching (DB), the number-average molecular weight ($M_n$), and the number of hydroxyl groups per HPG molecule ($n_{OH}$) were calculated from the $^{13}$C-NMR spectra using the following formulas reported previously.

$$DB = \frac{2D}{2D + L_{13} + L_{14}} \quad (1)$$

$$DP = \frac{T + L_{13} + L_{14} + D}{T - D} f_c \quad (2)$$

$$M_n = DP \times M_n(\text{glycidol}) + M_n(TMP) \quad (3)$$

$$n_{OH} = \frac{2T + L_{13} + L_{14}}{T + L_{13} + L_{14} + D} \times \frac{M_n(HPG) - M_n(TMP)}{M_n(\text{glycidol})} \quad (4)$$

where D, $L_{13}$, $L_{14}$, and T correspond to fractional peak intensities in the $^{13}$C-NMR spectra for dendritic, linear 1,3-unit, linear 1,4-unit, and terminal carbons of HPG, respectively, and $f_C$ is the functionality of the core molecule, TMP, which is three (FIG. 7-1~7-3). The molecular weight was alternatively determined by gel permeation chromatography (Agilent 1200S).

Rheological behavior of HPG (20%) with varying $M_w$ was evaluated by measuring the change in shear viscosity in response to varying shear rate using a rotating-disk rheometer (Kinexus, Malvern). The rotating shear rate was controlled from 0.01 to 100 s$^{-1}$. As a control, linear poly (ethylene glycol) having similar molecular weights (Sigma Aldrich) at the same concentration were examined.

Figures 2, 3, 4, 5, 6, 7, 8:
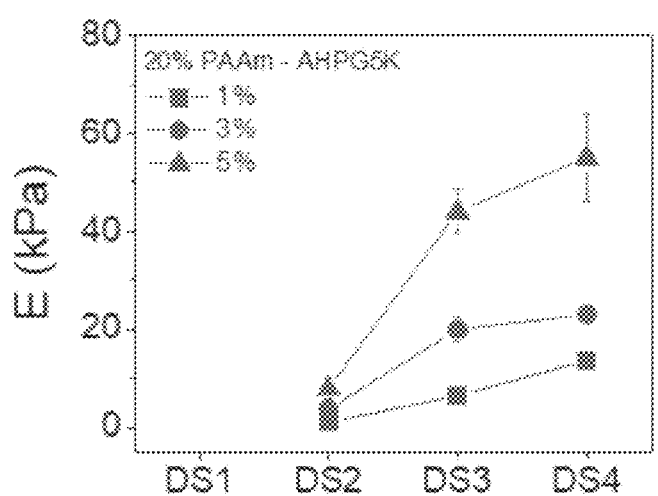
Figures 2, 3, 4, 5, 6, 7, 8, 9:
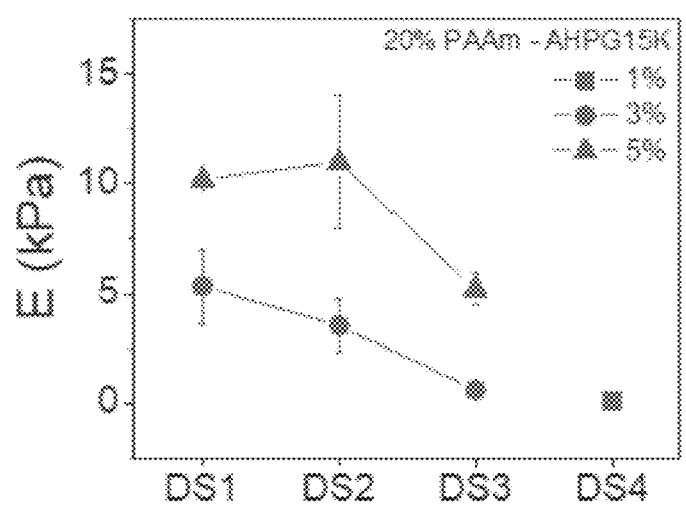
Figures 1, 3:
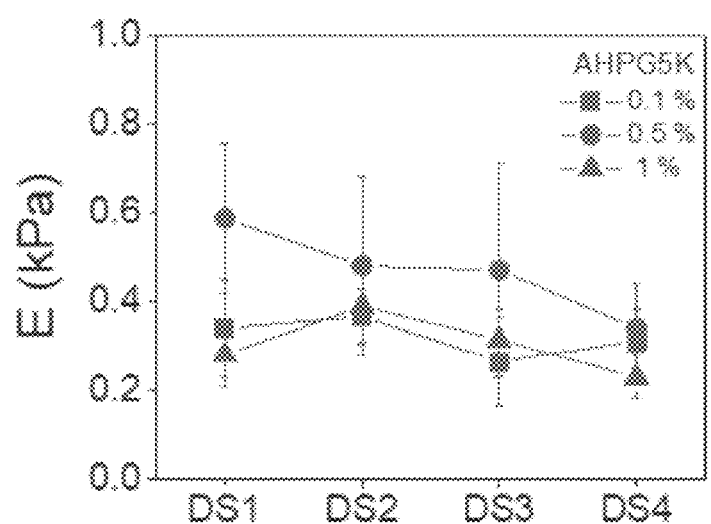
Figures 2, 3:
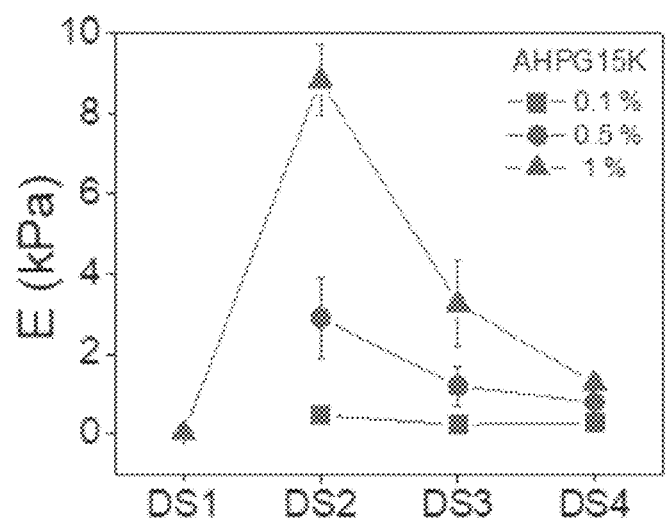
Figure 3:
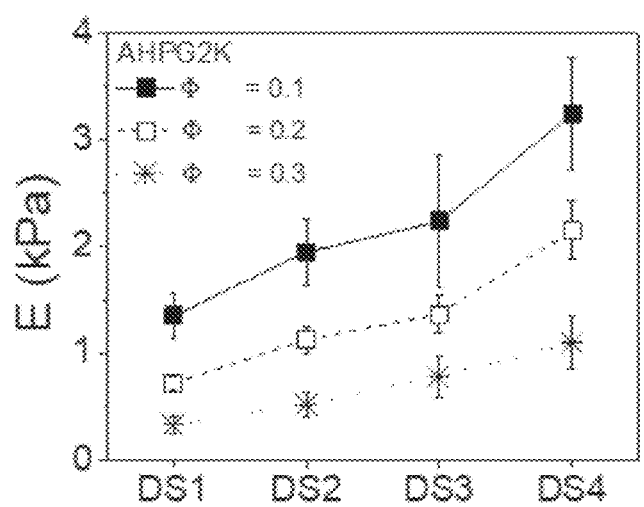
Figures 3, 4:
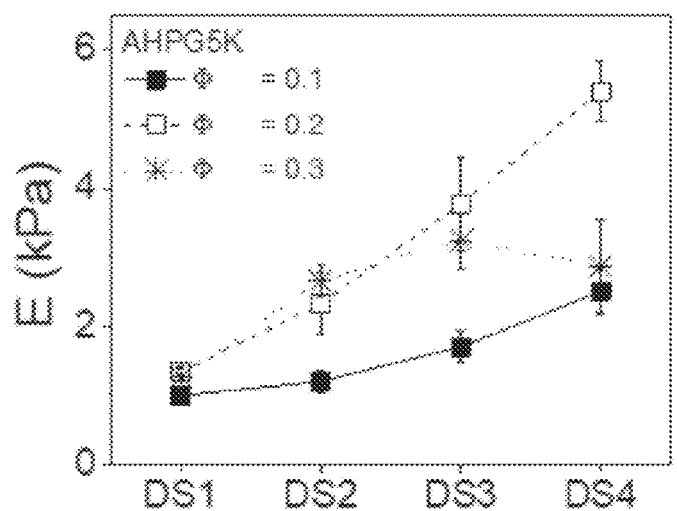
Figures 3, 4, 5:
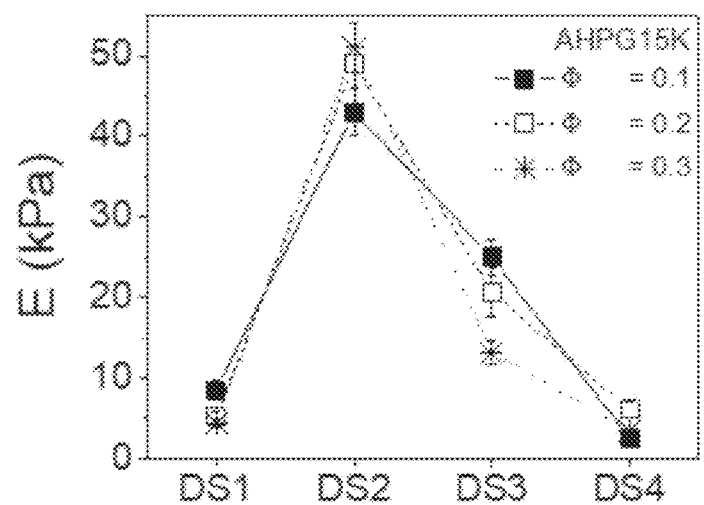
Figures 1, 4:
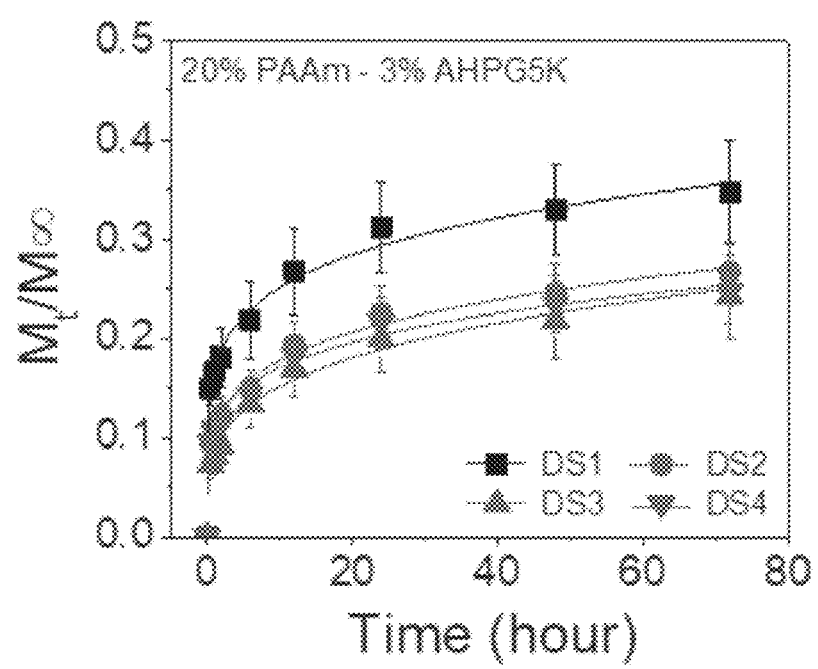
Figures 2, 4:
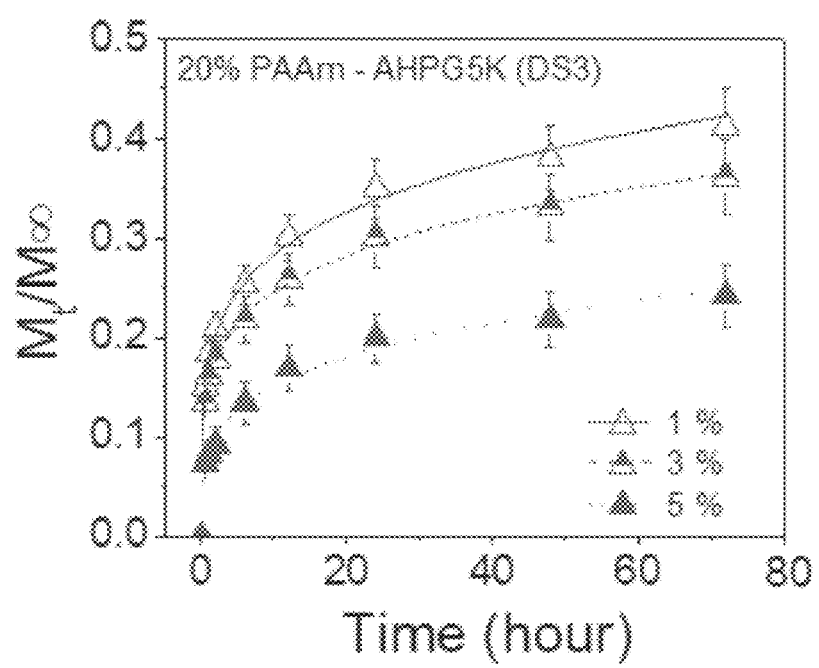
Figures 3, 4:
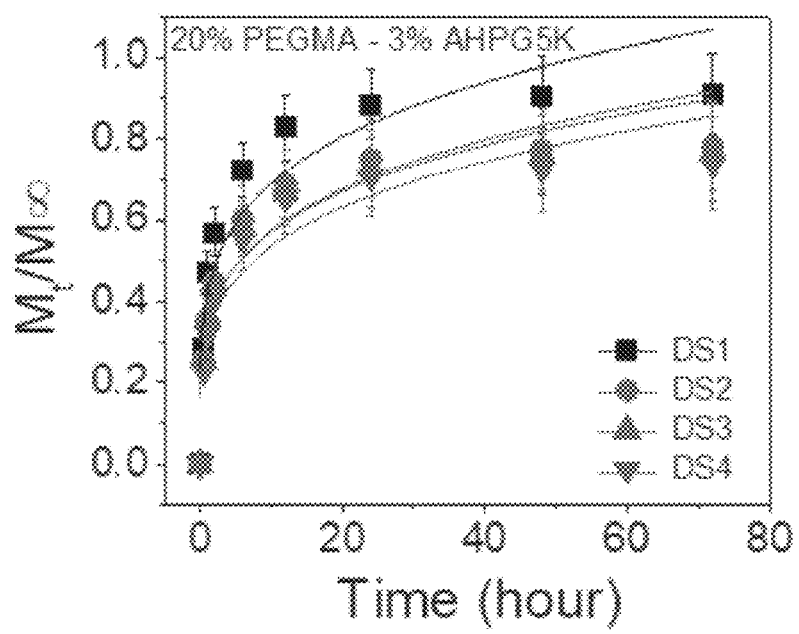
Figure 4:
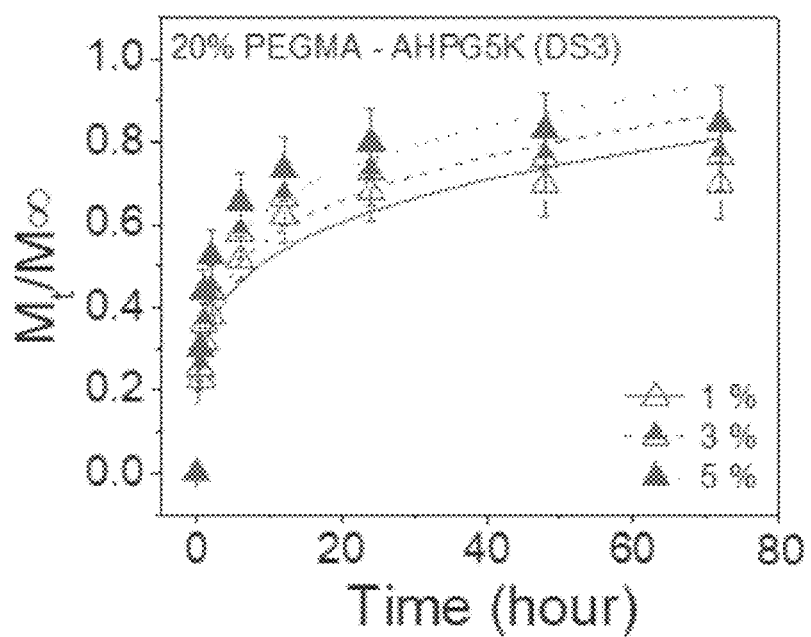
Figures 4, 5:
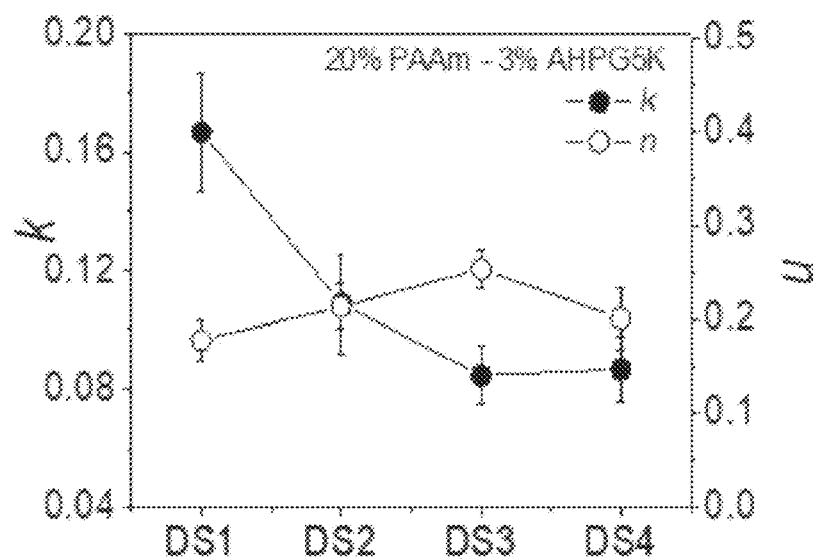
Figures 4, 5, 6:
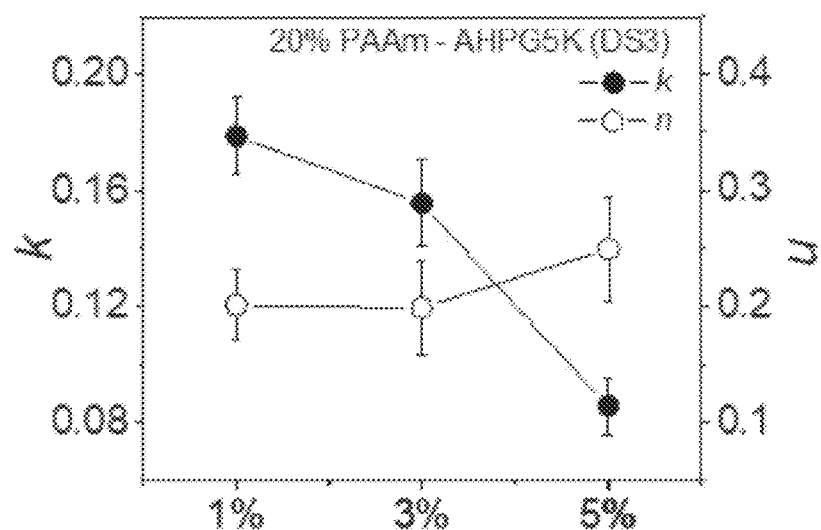
Figures 4, 5, 6, 7:
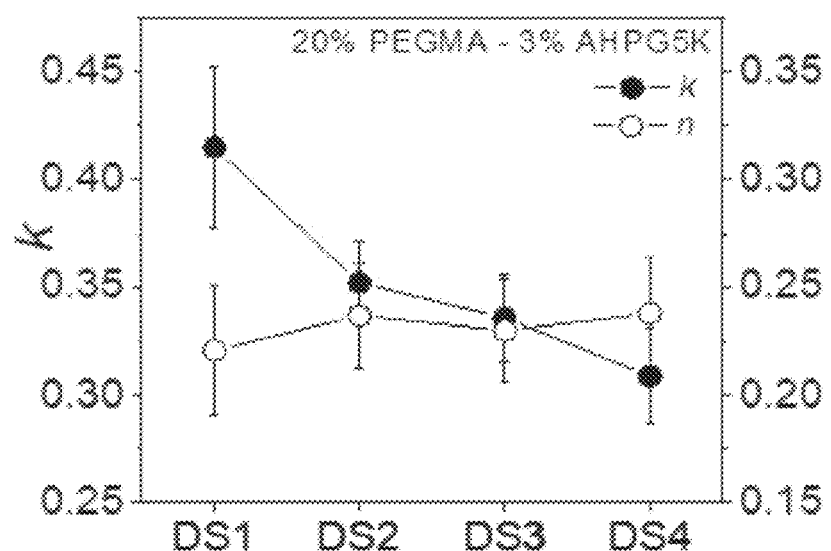
Figures 4, 5, 6, 7, 8:
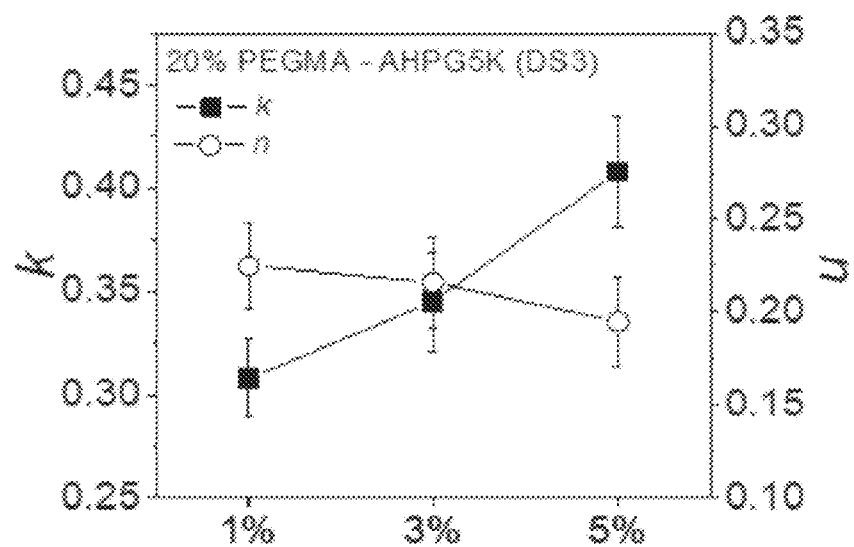
Figures 1, 5:
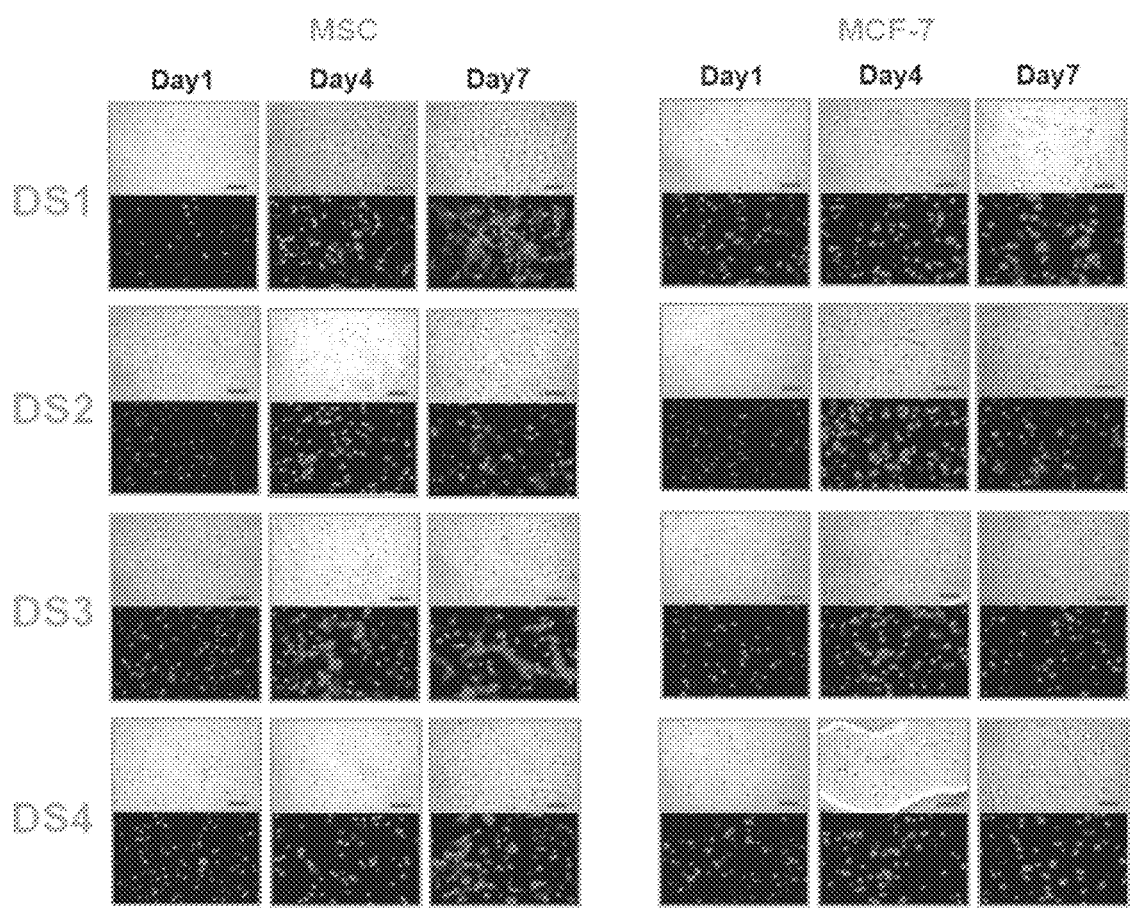
Figures 2, 5:
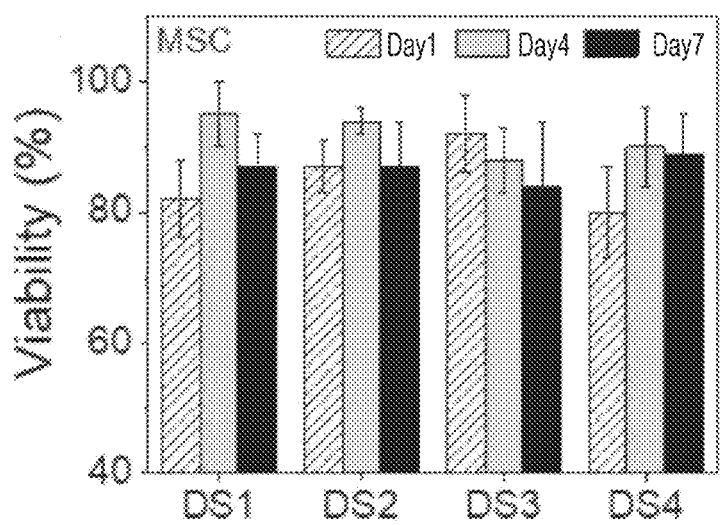
Figures 3, 5:
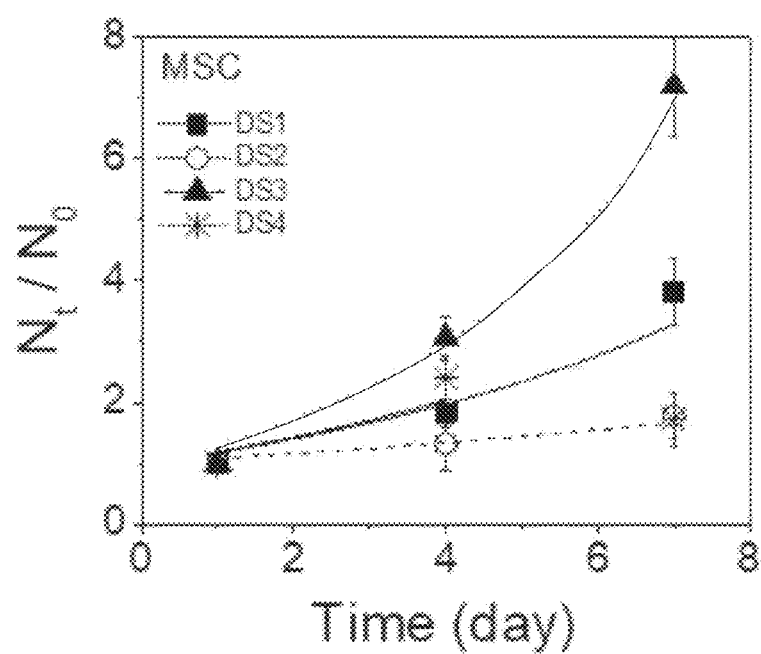
Figures 4, 5:
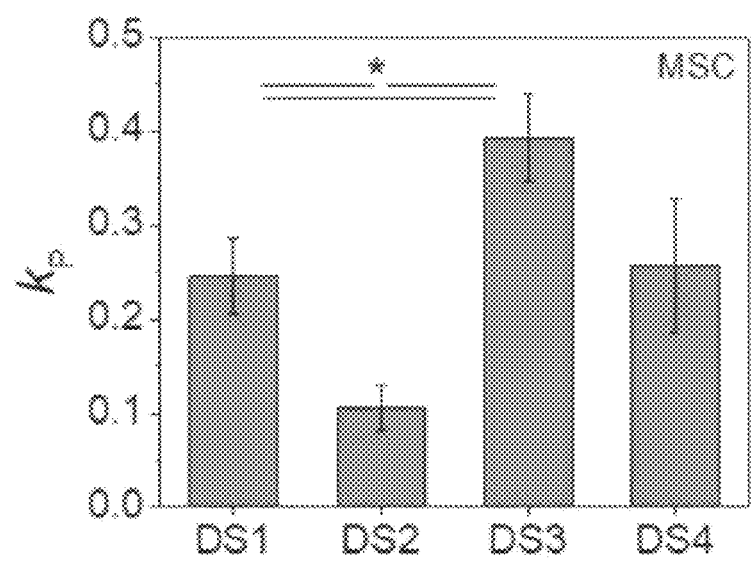
Figure 5:
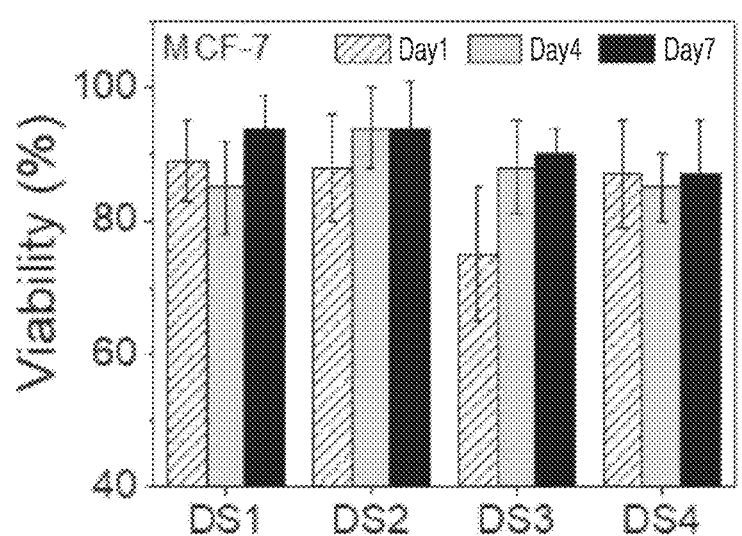
Figures 5, 6:
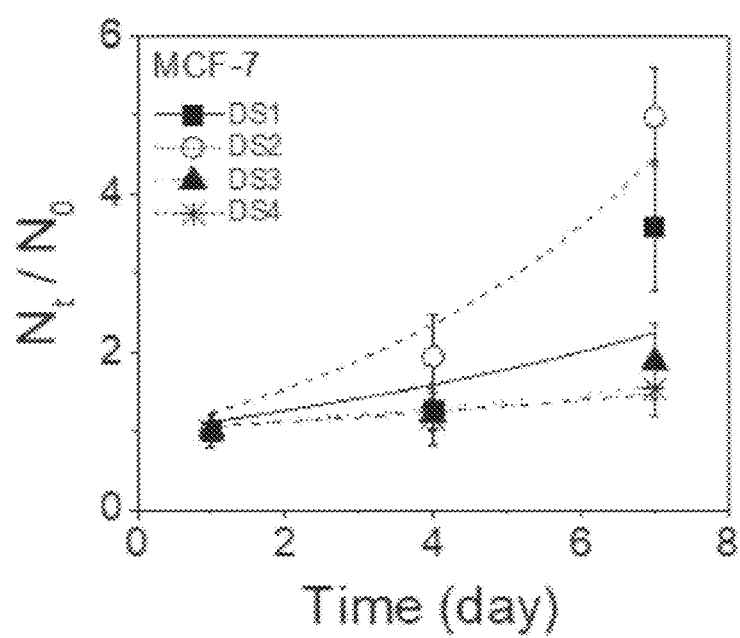
Figures 5, 6, 7:
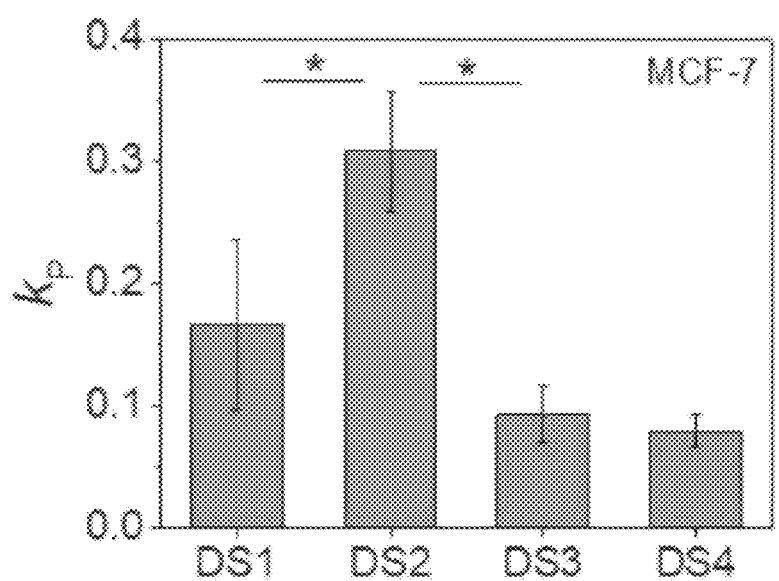
Figures 1, 6:
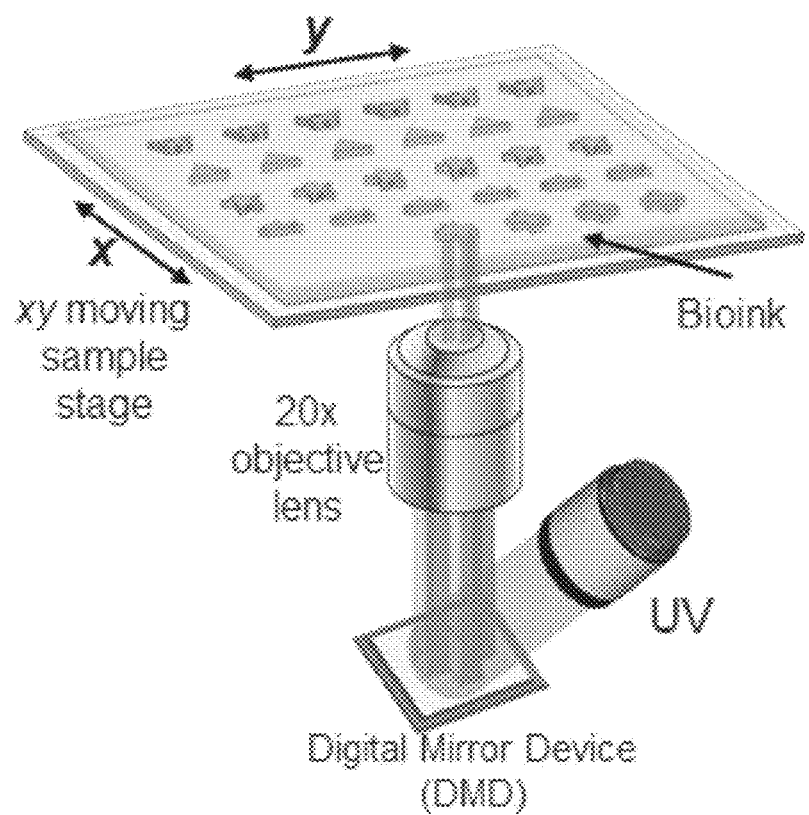
Figures 2, 6:
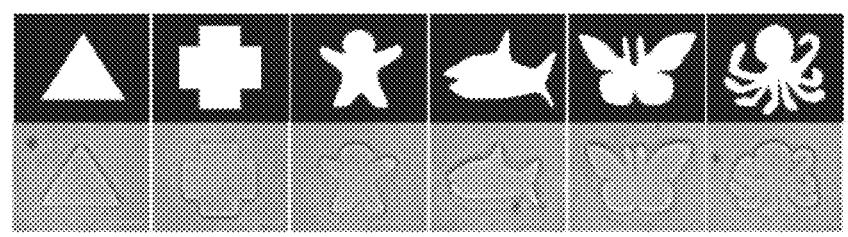
Figures 3, 6:
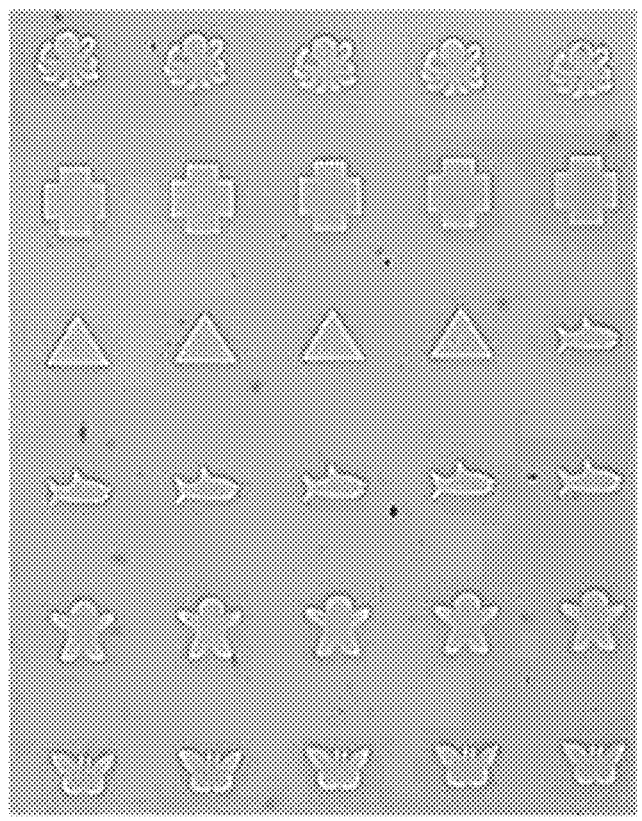
Figures 4, 6:
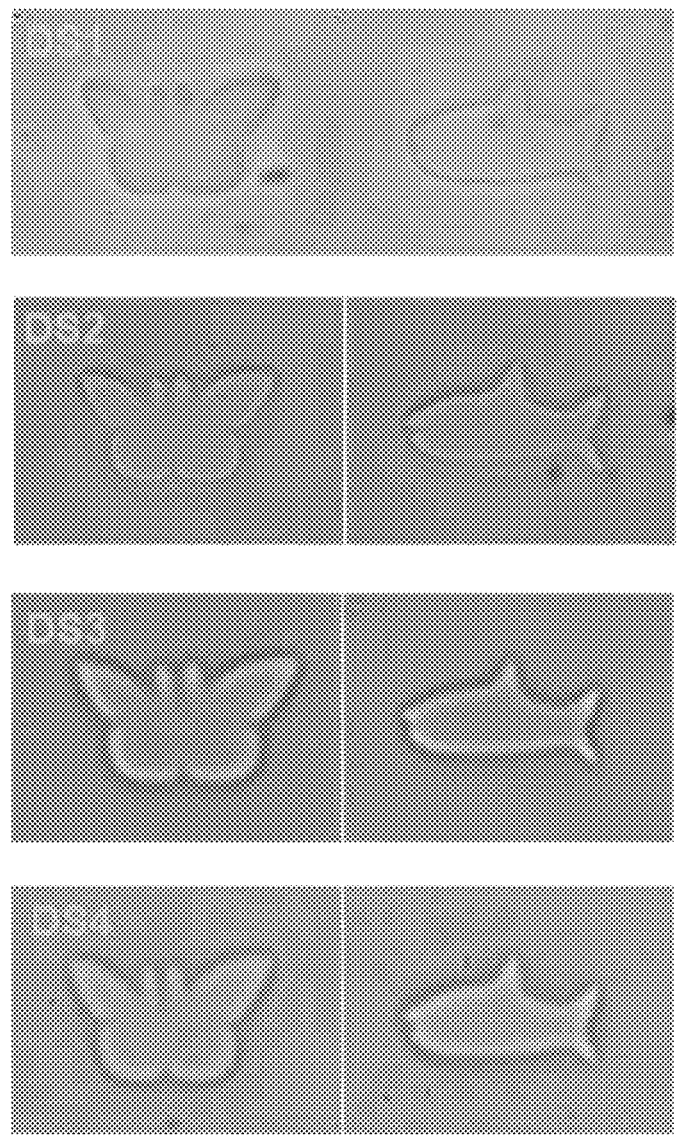
Figures 1, 7:
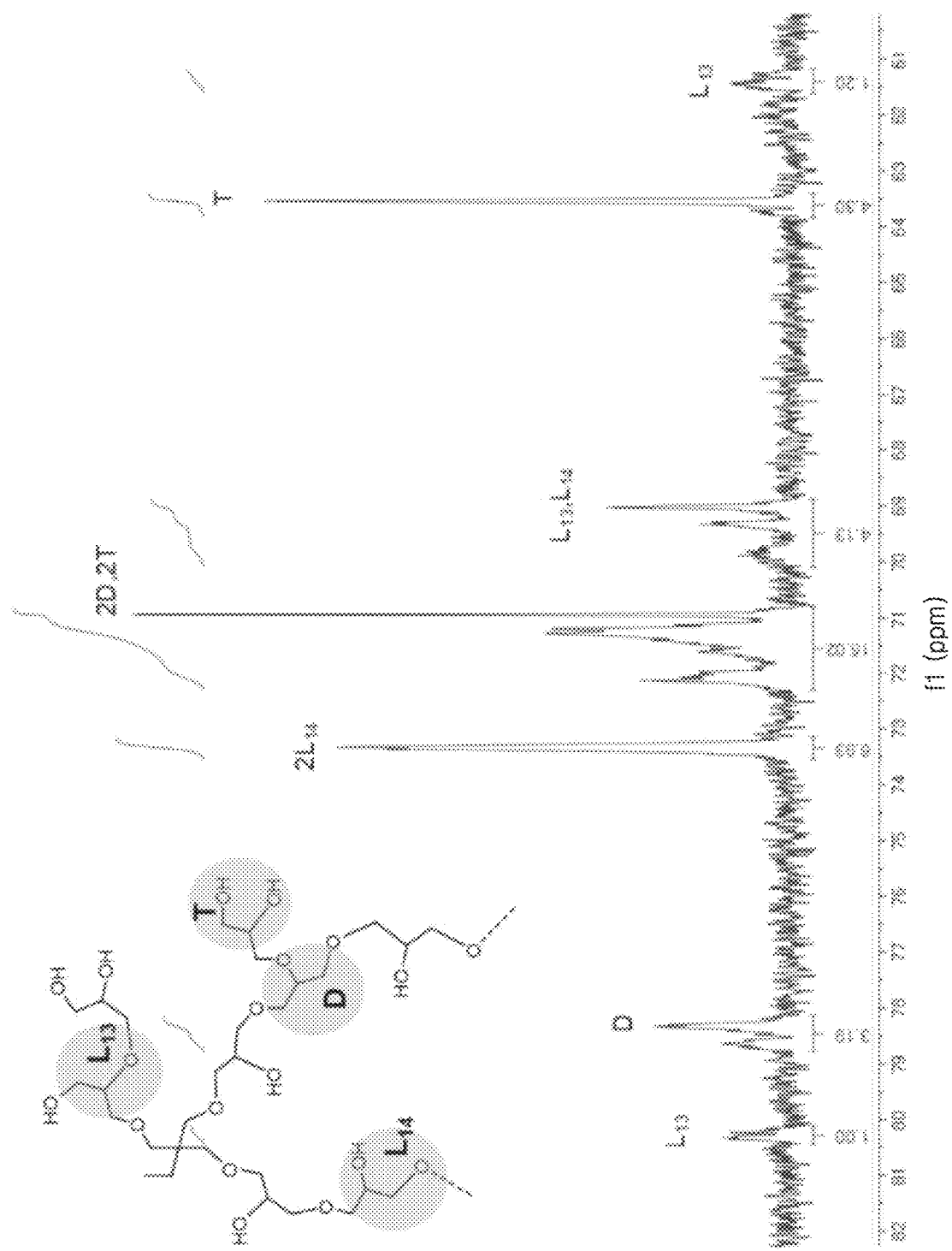
Figures 2, 7:
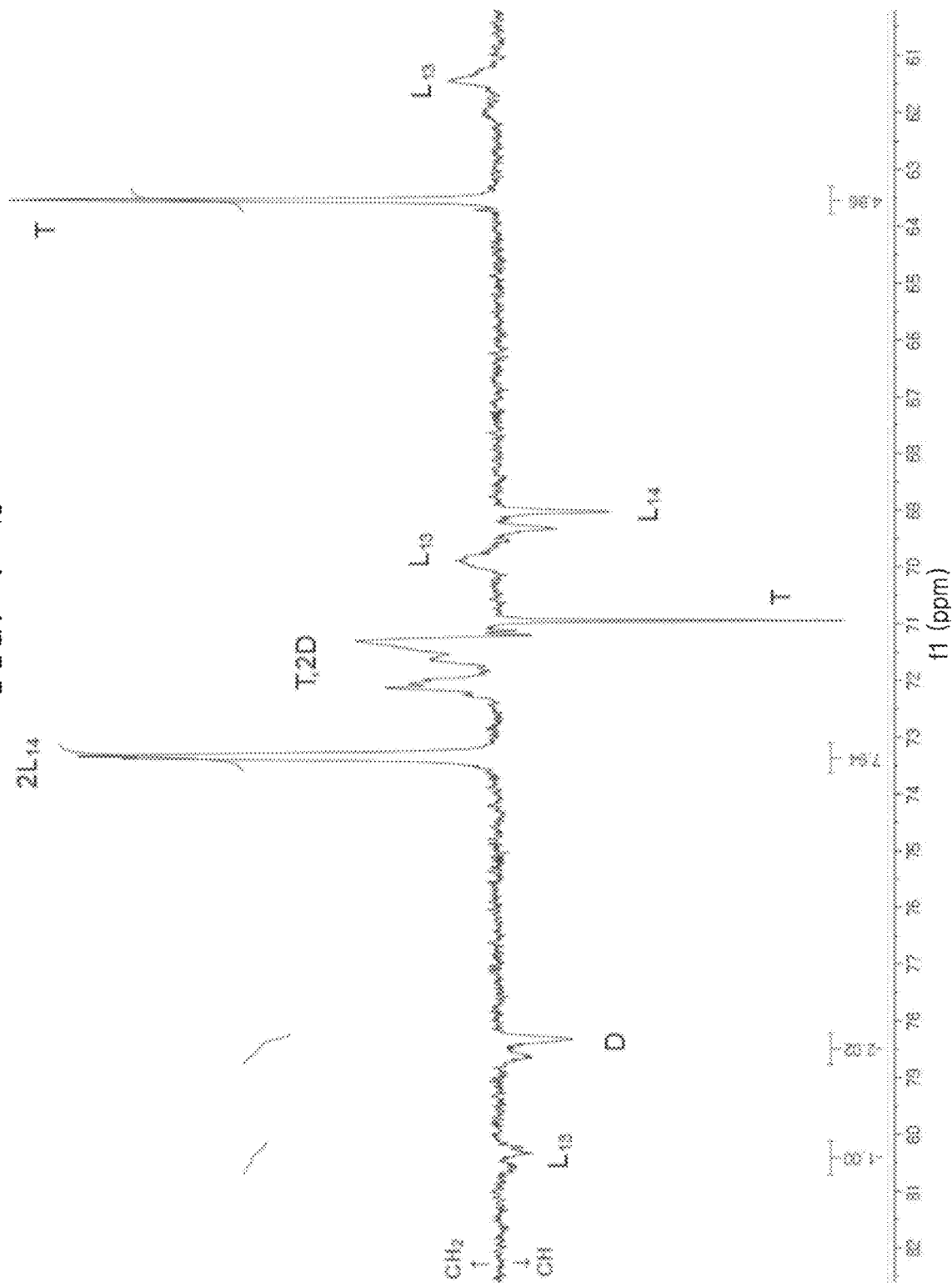
Figure 8:
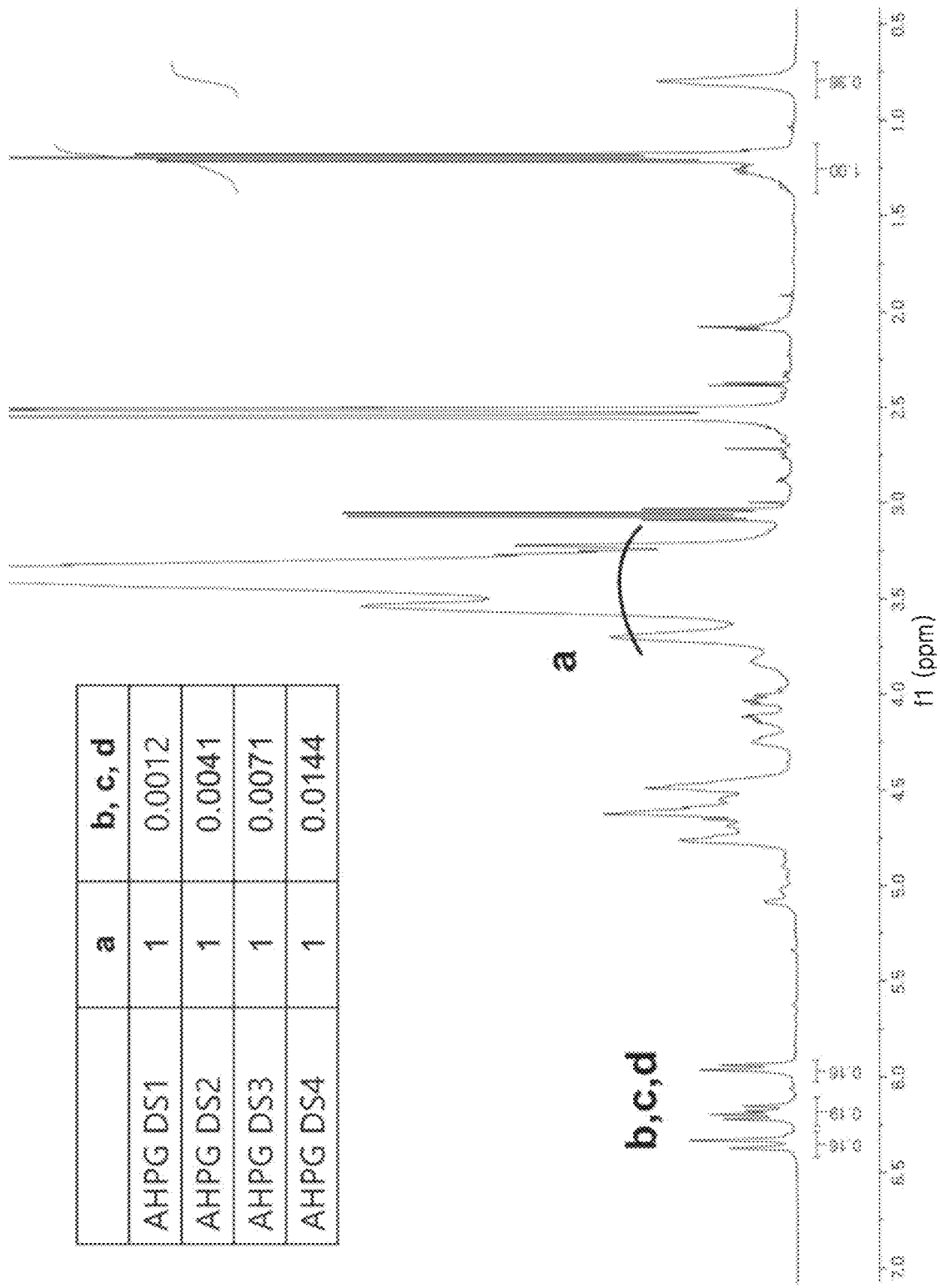

To bond acrylic functional groups to HPG, HPG and triethylamine (Sigma Aldrich) were first dissolved in dimethyl sulfoxane (Samchun Chemicals, Korea), followed by dropwise addition of acryloyl chloride. The mixture was stirred for 24 hours under dry $N_2$. The insoluble salt being formed was removed by filtration, and the crude product was obtained by precipitation in dry diethyl ether (Samchun Chemicals, Korea). The final product, acrylic HPG (AHPG), was obtained by extensive dialysis against deionized water and lyophilization. The DS of acrylate on HPG was controlled by varying the feed molar ratio of acryloyl chloride to the hydroxyl groups of HPG: 0.1, 0.3, 0.5, and 0.7. The presence and the degree of acrylate substitution of AHPG were assessed by $^1$H-NMR spectra (FIG. 8).

Fabrication of AHPG-Crosslinked Hydrogels

Hydrogel precursor solution was first prepared by adding varying concentrations of monomer and AHPG to phosphate buffered saline (PBS, pH 7.4) with 0.2% (w/v) 2-hydroxy-4'-(2-hydroxyethoxy)-2-methylpropiophenone (Sigma Aldrich) as a photoinitiator.

The monomers used herein were PEGMA ($M_n$ 500, Sigma Aldrich), acrylamide (Sigma Aldrich), and MGel.

For PEGMA and acrylamide, their concentrations were either about 10% (w/v) or about 20% (w/v), while varying the AHPG concentration from about 1% (w/v) to about 5% (w/v). For MGel, the concentration was fixed at 4% (w/v) while varying the AHPG concentration from 0.5% (w/v) to 3% (w/v). Alternatively, the total polymer concentration was kept constant at 10% (w/v) while varying the ratio of MGel and AHPG: 9:1, 8:2, and 7:3.

Each precursor solution was placed in between two glass plates with 0.5 mm spacer, and irradiated with UV for 2 min (intensity: 200 mW, emission filter about 250 nm to about 450 nm, distance: 5 cm, Model S1500, Omnicure®), resulting in hydrogel formation. Disk-shaped hydrogel samples were punched out (8 mm diameter) and incubated in PBS at 37° C. for 24 hours before characterization.

Mechanical Properties of AHPG-Crosslinked Hydrogels

The elastic moduli of AHPG-crosslinked hydrogels were calculated from stress-strain relationships obtained from uniaxial compression (Model 3343, Instron). Briefly, a hydrogel disk was compressed at a rate of 1 mm min$^{-1}$, and the elastic modulus was calculated as the slope of the stress-strain curve at the initial 10% strain, where the curve remained linear (i.e., elastic region). The swelling ratios of the hydrogels were calculated as the weight ratio of swollen hydrogel to the dried gel mesh.

Drug Release Kinetics

The time-dependent drug release behavior from various AHPG-crosslinked hydrogels was evaluated. Bovine serum albumin (BSA, 3 mg mL$^{-1}$, Sigma Aldrich) as a model drug was encapsulated into the hydrogel by incorporating into the gel precursor solution before hydrogel fabrication. The hydrogel disks (8 mm) were prepared as described above, and each hydrogel disk was incubated in 1 mL PBS at 37° C. At designated time points, the amount of BSA released into the surrounding PBS was measured using a commercially available protein assay kit (BCA™ Protein Assay, Thermo Fisher). The cumulative drug release profile overtime was plotted, and fitted with the following Ritger-Peppas model.

$$\frac{M_t}{M_\infty} = k_1 \cdot t^n \tag{5}$$

where $M_t$ was the amount of drug released at a time, t, $M_\infty$ was the total amount of encapsulated drug, k was the kinetic rate constants, and n was the exponent related to the release mechanism.

Three-Dimensional (3D) Cell Culture:

3D cell culture in AHPG-crosslinked hydrogel was performed and the viability and proliferation of the encapsulated cells were evaluated. Briefly, cells were suspended in a precursor solution at 2×10$^8$ cells mL$^{-1}$. The hydrogel disks were fabricated as described above (thickness: 0.3 mm, diameter 5 mm), and incubated in the cell culture media (Dulbecco's modified Eagle medium), supplemented with 10% fetal bovine serum and 1% penicillin/streptomycin at 37° C. with 5% atmospheric $CO^2$. At various times up to day 7, the viability of the encapsulated cells was obtained using LIVE/DEAD Cell Viability Assay (Thermo Fisher), following the manufacturer's instructions.

The proliferation rate ($k_P$) of encapsulated cells was calculated by counting the number of live cells at various times, and fitting the plot of normalized number of viable cells ($N_t/N_0$) with time (t) with the following power-law equation.

$$\frac{N_t}{N_0} = 2^{k_p \cdot t} \tag{6}$$

$N_t$ was the number of live cells at time, t, and N0 was the initial number of live cells measured right after gelation (t=0). Two cell types, MCF-7 (human breast adenocarcinoma cells) and D1 (murine mesenchymal stem cells) purchased from ATCC, were used herein.

Fabrication of Cell-Laden Microgels Using DLP Projection Printing

The AHPG-crosslinked hydrogel having desired shapes in micrometer scale was developed using a microscopic DLP projection printing. The system consisted of (1) a DMD chip (Texas Instruments), (2) DMD control software (DMD LightCrafter), and (3) a UV LED light (Thorlabs), assembled on an inverted microscope (Eclipse Ti-E, Nikon), which allowed simultaneous monitoring during the fabrication.

For a typical fabrication process, a gel precursor solution in between two glass slides was placed on a sample stage. The UV light (output power 4.5 mW) reflected off the DMD chip was directed to the sample stage via a 20× objective lens (S Plan Fluor ELWD, Nikon) for 45 seconds, resulting in microgel formation. The image of desired shape and size of the microgel was created using LabVIEW and then transferred to the DMD control software. The cell-laden microgels were cultured and analyzed for viability and proliferation, as described above.

An ink composition for bioprinting according to an embodiment can generate a hydrogel having a wide range of mechanical properties by controlling the molecular weight ($M_w$) and acrylate DS of AHPG, and when a drug is encapsulated in the ink composition for bioprinting, the resultant can be used in the drug delivery system, and when cells are encapsulated in the ink composition for bioprinting, the resultant ink composition can be used as miniaturized tissue constructs for biomedical applications.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. An ink composition for a hydrogel consisting of:
a poly(ethylene glycol)methacrylate (PEGMA) or methacrylic gelatin (MGel);
acrylic hyperbranched ployglycerol (AHPG);
an aqueous solvent; and
a photoinitiator,
wherein the AHPG has a weight-average molecular weight of more than 2000 Da to 15000 Da.

2. The ink composition of claim 1, wherein the concentration of AHPG is from about 0.1% (w/v) to 5% (w/v) based on the total volume of the ink composition.

3. The ink composition of claim 1, wherein the concentration of the PEGMA or MGel is from about 1% (w/v) to 30% (w/v) based on the total volume of the ink composition.

4. The ink composition of claim 1, wherein the sum of the concentration of the PEGMA or MGel and the concentration of AHPG is from about 5% (w/v) to about 30% (w/v) based on the total volume of the ink composition.

5. The ink composition of claim 1, wherein, in the AHPG, an acrylic group is linked to hyperbranched polyglycerol via an ester bond.

6. The ink composition of claim 5, wherein the acrylic group is acrylate or methacrylate.

7. The ink composition of claim 1, wherein the aqueous solvent is phosphate buffered saline (PBS).

8. The ink composition of claim 1, wherein the AHPG is prepared by reacting glycidol with polyhydric alcohol to produce hyperbranched polyglycerol, and reacting the OH end of the prepared hyperbranched polyglycerol with a compound having an acryl group.

9. The ink composition of claim 8, wherein the polyhydric alcohol is a trivalent to pentavalent alkanol.

10. The ink composition of claim 8, wherein the OH end of the hyperbranched polyglycerol reacting with the compound having an acryl group is from about 5% to about 80% of all of the OH ends of the hyperbranched polyglycerol.

11. The ink composition of claim 1, wherein the PEGMA or MGel has a number-average molecular weight of about 400 Da to about 50000 Da.

12. The ink composition of claim 1, wherein the ink composition has a shear-thinning property.

13. A crosslinked hydrogel formed by irradiating light to the ink composition of claim 1.

14. The hydrogel of claim 13, wherein the hydrogel further comprises a drug.

15. The hydrogel of claim 13, wherein the hydrogel further comprises cells and is used as a scaffold for cell culturing for tissue engineering.

* * * * *